(12) United States Patent
Vestal et al.

(10) Patent No.: US 10,089,586 B2
(45) Date of Patent: Oct. 2, 2018

(54) JOB MANAGEMENT SYSTEM FOR A FLEET OF AUTONOMOUS MOBILE ROBOTS

(71) Applicant: Omron Adept Technologies, Inc., San Ramon, CA (US)

(72) Inventors: Matthew Vestal, Keene, NH (US); Matthew LaFary, Peterborough, NH (US); Peter Stopera, Hollis, NH (US)

(73) Assignee: OMRON ADEPT TECHNOLOGIES, INC., San Ramon, CA (US)

( * ) Notice: Subject to any disclaimer, the term of this patent is extended or adjusted under 35 U.S.C. 154(b) by 941 days.

(21) Appl. No.: 14/370,383

(22) PCT Filed: Feb. 8, 2013

(86) PCT No.: PCT/US2013/025336
§ 371 (c)(1),
(2) Date: Jul. 2, 2014

(87) PCT Pub. No.: WO2013/119942
PCT Pub. Date: Aug. 15, 2013

(65) Prior Publication Data
US 2014/0365258 A1    Dec. 11, 2014

Related U.S. Application Data

(60) Provisional application No. 61/596,685, filed on Feb. 8, 2012.

(51) Int. Cl.
*G06Q 10/00*   (2012.01)
*G06Q 10/06*   (2012.01)
*G05D 1/02*    (2006.01)

(52) U.S. Cl.
CPC ... *G06Q 10/063114* (2013.01); *G05D 1/0274* (2013.01); *G05D 1/0297* (2013.01);
(Continued)

(58) Field of Classification Search
None
See application file for complete search history.

(56) References Cited

U.S. PATENT DOCUMENTS 4,674,048 A   6/1987   Okumura
4,727,492 A   2/1988   Reeve et al.
(Continued)

FOREIGN PATENT DOCUMENTS

EP           78357 A2      1/2011
JP      07-281753 A      10/1995
(Continued)

OTHER PUBLICATIONS

Nuchter A. et al: "Towards Semantic Maps for Mobile Robots", Robotics and Autonomous Systems, Elsevier Science Publishers, Amsterdam, NL, vol. 56, No. 11, Nov. 30, 2008, pp. 915-926.
(Continued)

*Primary Examiner* — Stephanie Z Delich
(74) *Attorney, Agent, or Firm* — Murphy, Bilak & Homiller, PLLC

(57) ABSTRACT

The Job Management System (JMS) of the present invention processes job requests in an automated physical environment, such as a factory, hospital, order processing facility or office building, wherein the job requests are handled by a fleet of autonomously-navigating mobile robots. The JMS includes a map defining a floor plan, a set of virtual job locations and a set of one or more virtual job operations associated with virtual job locations. The JMS automatically determines the actual locations and actual job operations for the job requests, and intelligently selects a suitable mobile robot to handle each job request based on the current status and/or the current configuration for the selected mobile robot. The JMS also sends commands to the selected mobile robot to cause the mobile robot to automatically drive the
(Continued)

actual job location, to automatically perform the actual job operations, or both.

69 Claims, 15 Drawing Sheets

(52) U.S. Cl.
CPC ........... *G05D 1/024* (2013.01); *G05D 1/0246* (2013.01); *G05D 1/0255* (2013.01); *G05D 2201/0211* (2013.01); *G05D 2201/0216* (2013.01); *Y10S 901/01* (2013.01)

(56) References Cited

U.S. PATENT DOCUMENTS

| | | |
|---|---|---|
| 4,763,055 A | 8/1988 | Daggett et al. |
| 5,279,672 A | 1/1994 | Betker et al. |
| 5,324,948 A | 1/1994 | Dudar et al. |
| 5,559,696 A | 9/1996 | Borenstein |
| 5,610,815 A | 3/1997 | Gudat et al. |
| 5,764,014 A | 6/1998 | Jakeway et al. |
| 5,897,595 A | 4/1999 | Hawkins et al. |
| 5,931,875 A | 8/1999 | Kemner et al. |
| 6,496,755 B2 | 12/2002 | Wallach et al. |
| 6,580,246 B2 | 6/2003 | Jacobs |
| 6,614,427 B1 | 9/2003 | Aubrey |
| 6,667,592 B2 | 12/2003 | Jacobs et al. |
| 6,748,292 B2 | 6/2004 | Mountz |
| 6,853,877 B1 | 2/2005 | Slater et al. |
| 6,895,301 B2 | 5/2005 | Mountz |
| 7,082,350 B2 | 7/2006 | Skoog |
| 7,117,068 B2 | 10/2006 | Critchlow |
| 7,135,991 B2 | 11/2006 | Slemmer et al. |
| 7,272,467 B2 | 9/2007 | Goncalves et al. |
| 7,456,596 B2 | 11/2008 | Goodall et al. |
| 7,532,113 B2 | 5/2009 | Horvitz et al. |
| 7,650,013 B2 | 1/2010 | Dietsch et al. |
| 7,693,654 B1 | 4/2010 | Dietsch et al. |
| 7,729,801 B2 | 6/2010 | Abromson |
| 7,894,393 B2 | 2/2011 | Zini et al. |
| 7,912,633 B1 | 3/2011 | Dietsch et al. |
| 8,169,596 B2 | 5/2012 | Weiss et al. |
| 8,688,275 B1 | 4/2014 | LaFary et al. |
| 2002/0049530 A1 | 4/2002 | Poropat |
| 2003/0030398 A1 | 2/2003 | Jacobs |
| 2004/0073337 A1 | 4/2004 | McKee et al. |
| 2005/0047895 A1 | 3/2005 | Lert, Jr. |
| 2006/0015215 A1 | 1/2006 | Howard et al. |
| 2006/0184279 A1* | 8/2006 | Okamoto ............... B25J 5/007 700/245 |
| 2006/0195226 A1 | 8/2006 | Matsukawa et al. |
| 2006/0265103 A1 | 11/2006 | Orita |
| 2007/0112461 A1 | 5/2007 | Zini et al. |
| 2007/0140821 A1 | 6/2007 | Garon et al. |
| 2007/0192910 A1 | 8/2007 | Vu et al. |
| 2007/0294029 A1 | 12/2007 | D'Andrea et al. |
| 2008/0009969 A1 | 1/2008 | Bruemmer et al. |
| 2009/0187278 A1* | 7/2009 | Zhuk ................... G05D 1/0088 700/246 |
| 2009/0234499 A1 | 9/2009 | Nielsen et al. |
| 2009/0281661 A1 | 11/2009 | Dooley et al. |
| 2010/0049364 A1 | 2/2010 | Landry et al. |
| 2010/0094459 A1 | 4/2010 | Cho et al. |
| 2011/0054689 A1 | 3/2011 | Nielsen et al. |
| 2011/0137457 A1 | 6/2011 | Zini |

FOREIGN PATENT DOCUMENTS

| | | |
|---|---|---|
| JP | 2007122304 A | 5/2007 |
| WO | 2009040777 A2 | 4/2009 |

OTHER PUBLICATIONS

V. Sequeira et al: "Automated Reconstruction of 3D Models from Real Environments", ISPRS Journal of Photogrammetry and Remote Sensing, vol. 54, No. 1, Feb. 1, 1999, pp. 1-22.
Evans. "Help Mate, The Trackless Robotic Courier: A Perspective on the Development of a Commercial Autonomous Mobile Robot," Lecture Notes in Control and Information Sciences, 1998. vol. 236, p. 182-210.
Thrun et al. "Robust Monte Carlo Localization for Mobile Robots," Artificial Intelligence, Apr. 20, 2000. vol. 128, No. 1-2, p. 99-141.
Wolf et al. "Robust Vision Based Localization by Combining and Image Retrieval System with Monte Carlo Localization," IEEE Transactions on Robotics, Apr. 2005. vol. 21, No. 2, p. 208-216.
Weiss et al. "Keeping Track of Position and Orientation of Moving Indoor Systems by Correlation of Range-Finder Scans," Proceedings of the IEEE/RSJ/GI International Conference on Intelligent Robots and Systems, 1994. vol. 1, p. 595-601.
Thrun et al. "Learning Maps for Indoor Mobile Robot Navigation," School of Computer Science, Apr. 14, 1996.
Thrun et al. "A Probabilistic Approach to Concurrent Mapping and Localization for Mobile Robots," Machine Learning and Autonomous Robots, 31/5 ed., Kluwer Academic Publishers, Boston, Mar. 14, 1998.
Thrun et al. "A Probabilistic Online Mapping Algorithm for Teams of Mobile Robots," International Journal of Robotics, 2001. vol. 20(5), p. 335-363.
Thrun et al. "Map Learning and High-Speed Navigation in RHINO," Carnegie Mellon University, 1997.
Thrun et al. "An Approach to Learning Mobile Robot Navigation," Robotics and Autonomous Systems, Mar. 1995.
Fox et al. "Active Markov Localization for Mobile Robots," Mar. 19, 1998.
Liu et al. "Using EM to Learn 3D Models with Mobile Robots," Eighteenth International Conference on machine Learning, Jun. 28, 2001.
Gutmann et al. "Incremental Mapping of large Cyclic Environments," Proceedings of the IEEE International Symposium on Computational Intelligence in Robotic and Automation, 2000.

* cited by examiner

```
2D-Map
MapInfo: DockType "Name=Dock" "Label=Dock" "NameRequired=1"
MapInfo: GoalType "Name=Goal" "Label=Goal" "NameRequired=1" "Color0=0xfff00" "Heading=Required"
MapInfo: SectorType "Name=ResistedSector" "Label=ResistedSector" "Desc=Area that the robot will try to avoid, but will
drive through if necessary." "NameRequired=1" "Color0=0xf2ea72" "Color1=0xbea4ce" "NameRequired=1"
MapInfo: SectorType "Name=TwoWayDriveOnRightSector" "Label=PreferredDirectionRight" "Desc=Two Way Drive on Right"
"NameRequired=1" "Color0=0xad43b4" "Color1=0x91b899" "Shape=GradTwoWayDriveOnRight" "NameRequired=1"
Cairn: ResistedSector 0 0 0.000000 "" ICON "ResistedSector17" -22940 -14446 -14715 -12764
Cairn: ResistedSector 0 0 0.000000 "" ICON "ResistedSector14" -22794 -12582 -7732 -10205
Cairn: GoalWithHeading -20215 -8485 -87.982000 "" ICON "Mechanical"
Cairn: ResistedSector 0 0 0.000000 "" ICON "ResistedSector18" -18240 -10369 -14050 -9911
Cairn: Goal -13843 -3056 0.000000 "" ICON "Software"
Cairn: ResistedSector 0 0 0.000000 "" ICON "ResistedSector15" -12453 -10401 -9276 -9816
Cairn: ResistedSector 0 0 90.000000 "" ICON "ResistedSector13" -7824 15631 -6354 16802
Cairn: Goal -7126 -16086 0.000000 "" ICON "Empty Conference"
Cairn: Goal -5823 -7570 0.000000 "" ICON "BD Lab West Mid"
Cairn: GoalWithHeading -5693 -1653 135.145272 "" ICON "BD Lab West North"
Cairn: GoalWithHeading -3908 -28384 -179.800000 "" ICON "Offices"
Cairn: ResistedSector 0 0 0.000000 "" ICON "ResistedSector12" -1804 -10937 1082 -7773
Cairn: TwoWayDriveOnRightSector 0 0 0.000000 "" ID=13346 "PreferredDirectionRight1" 2271 -18108 14449 -13021
Cairn: ResistedSector 0 0 0.000000 "" ICON "ResistedSector16" 3896 -27097 6854 -25557
Cairn: GoalWithHeading 4195 -28833 -80.258274 "" ICON "Hall Entry"
Cairn: GoalWithHeading 5868 -10253 -90.000000 "" ICON "BD Mid"
Cairn: GoalWithHeading 17212 -1515 -90.000000 "" ID=3145776 "BD Northeast"
Cairn: Goal 18401 -17381 0.000000 "" ICON "Closet"
Cairn: GoalWithHeading 19220 -25601 -154.771535 "" ICON "Training"
Cairn: Goal 21597 -7451 0.000000 "" ICON "BD_comm_support"
LINES
-24163 -6218 -21563 -6227
-24148 -2057 -24162 -6218
-24141 168 -24148 -2057
-24096 -10015 -24097 -13709
-24096 -1842 -24096 -1843
```

FIG. 3

JOB MANAGEMENT SYSTEM FOR A FLEET OF AUTONOMOUS MOBILE ROBOTS

FIELD OF THE INVENTION

The present invention relates to systems and methods for processing job requests in an automated physical environment. More particularly, the present invention is directed to a job management system that receives and processes job requests in an automated physical environment, such as a warehouse, factory, hospital, office building, mail or online order processing facility, or similar enterprise, where the physical environment includes a fleet of mobile robots for automated handling of the job requests.

RELATED ART

In a typical order processing environment, merchandise may be transported around a distribution center or warehouse by human operators pushing, pulling or driving mobile containers, carriers, carts, cargo bins or fork lifts from one location to another. Using human operators to transport items from one location to another location in the physical environment in this manner has many disadvantages, including for example: problems keeping track of the physical locations of the transported items; difficulties moving items around the factory or warehouse according to schedules dictated by automated components in the order processing system; exposing the human operators to increased risks of physical injury or death; increased risk of damage to expensive or rare equipment and inventory; and exposing the transported items and manufacturing equipment to higher contamination levels caused by the presence of the human operators. In some environments, including automated manufacturing environments, instead of using humans to transport finished and unfinished articles and merchandise about the factory or warehouse, conveyor belts and/or overhead product transportation systems (e.g., a monorail system suspended from the ceiling) are used. The disadvantages of using conveyor belts and overhead transport systems include: being constrained to a fixed (linear) delivery path; not being able to deliver products to downstream workstations if an upstream workstation in the process is out of service; and having to move and/or make expensive changes to the conveyor belt system or overhead transportation system if a single workstation in the process has to be moved to a different location.

To help move materials between locations in the factory or warehouse more efficiently, fleets of mobile robots, also called automated guided vehicles (or "AGVs"), have been introduced to order processing centers, manufacturing facilities, hospitals and office buildings. But the utility and flexibility of conventional fleets of mobile robots for these environments has heretofore been very limited due to several significant operational shortcomings, including for instance: (1) having to install markers, rails, wires or grids in the floors, ceilings and/or walls of the facilities so that the fleet of mobile robots can use them for navigation; (2) the mobile robots in the fleet having little or no ability to independently determine their routes to specified destinations (i.e., to navigate autonomously); (3) the mobile robots in the fleet having little or no ability to modify a selected route to a specified destination in response to encountering other non-stationary objects, including people and other mobile robots while driving to the specified destination; and (4) the mobile robots in the fleet having little or no ability to automatically determine and carry out a particular task or operation upon arriving at a specified destination, to name but a few examples. Another significant shortcoming of existing mobile robot solutions is that they tend to rely on the mobile robots in the fleet being able to travel in perfectly straight lines. But factories, warehouses and distribution centers are usually not laid out in perfectly straight lines because they tend to expand outward from center in multiple directions and at different rates according to need and funding. Therefore, the existing mobile robot fleet solutions tend to be less useful, less efficient and less productive in situations where the tools and workstations that the fleet of mobile robots have to service have varying shapes and sizes, or are physically offset from one another.

Because of the above-described limitations and shortcomings associated with conventional mobile robot fleets, the conventional job management systems, which control and manage the fleets of mobile robots, have also been very limited in utility and flexibility. For example, many of the conventional job management systems must constantly monitor and control every aspect of every mobile robot's progress, with rigid and exacting specificity, explicitly instructing every mobile robot in the fleet on: (1) how to get to a specified destination and (2) when to perform a task once the intended destination is reached. A series of such instructions might include, for instance, the following commands:

"pick up cargo"
"back up 0.5 meters"
"rotate right 90 degrees;"
"drive 10 meters forward"
"rotate right 45 degrees;"
"drive 50 meters forward;"
"pause 7 seconds" (while another mobile robot passes by);
"drive 8 meters forward;"
"rotate left 60 degrees;"
"pause 5 seconds" (while another mobile robot passes by)
"drive 3 meters forward;"
"back up 0.2 meters;" and
"unload cargo"

Thus, the existing job management systems must not only distribute job requests to particular mobile robots in the fleet, but must also provide navigation, obstacle avoidance and traffic management functions for every robot in the fleet. The result is that, although useful to some degree, the conventional job management systems for fleets of mobile robots do not permit truly "intelligent" delegation, handling and completion of job requests within a given operating environment.

Another problem associated with existing automated warehouse management systems involving fleets of mobile robots is that they tend to use a fleet of homogeneous mobile robots, all having the same set of functions, capabilities and constraints. As a result, conventional job management systems tend to distribute job requests to the mobile robots in the fleet based on a very limited set of criteria, such as the mobile robot's current position in the physical environment relative to the specified job location for the job request. Thus, what is needed is a job management system for processing job requests in an environment wherein the mobile robots in the fleet are heterogeneous and have a diverse collection of capabilities and functions.

SUMMARY OF THE INVENTION

The job management system (JMS) of the present invention receives, coordinates and manages job requests in a physical environment, such as a factory, order processing facility, distribution center, hospital or office building. The job management system receives and prioritizes the job requests, and selects individual units from a fleet of one or more heterogeneous autonomously-navigating mobile robotic units to carry out the job requests. The job requests for the mobile robots may specify a virtual (i.e., mapped job location) representing an actual job location in the physical environment, a virtual (mapped) job operation representing an actual job operation in the physical environment, or both a virtual job location and a virtual job operation. The job management system automatically determines the actual job locations and job operations associated with the virtual job locations and operations, and automatically selects a suitable mobile robot from the fleet to handle each job request.

In some embodiments, the job management system selects the mobile robot to handle the job request based on the selected mobile robot's current status, the selected mobile robot's current configuration, or both the current status and the current configuration for the selected mobile robot. The job management system also sends one or more commands to the selected mobile robot to cause the selected mobile robot to automatically drive to the actual job location, if necessary, and to automatically perform the actual job operation. In some cases, the job management system sends one or more commands that cause the selected mobile robot to execute both steps of driving to the actual job location and performing the requested job operation.

The job operations may encompass any task suitable for performance by a mobile or industrial robot, including for example, picking up, transporting and dropping off objects and materials, as well as other tasks unrelated to transporting objects and materials, such as drilling, stamping or cutting an object, or cleaning up (sanitizing or disinfecting) an area. Accordingly, the mobile robots in the fleet may have different physical configurations, including, for example, being equipped with a variety of different conveyor belts, handlers, manipulators, support platforms, payload carriers, trailers or totes. The job management system and the mobile robots also may be configured to process a request to deliver a "digital payload" to a specified job location in the physical environment. For instance, if the job request calls for selecting a mobile robot having certain types of equipment (e.g., a sensor, camera, projector, x-ray machine, LCD display and/or speaker), then the job operation may include tasks such as recording or projecting light, sound or video data, or detecting and sampling wireless signals, toxic gases or liquids.

In preferred embodiments, for each job request received, the job management system selects an appropriate mobile robot from the fleet based the job request and the current statuses and configurations of the mobile robots in the fleet, and sends a command instruction to the selected mobile robot that causes the selected mobile robot to automatically drive to the appropriate job location, if necessary, and in some cases, automatically perform the specified job operation. In some scenarios, the fleet of mobile robots may be configured, for example, to perform one or more tasks according to the physical location where the mobile robot is summoned or sent. For example, in a security application, the system may be programmed such that when a robot outfitted with motion detection capability is sent to a certain location, the robot will plot a route to that location, travel to that location, and then turn on its motion detection equipment to start monitoring motion in that area.

In some embodiments, the job management system of the present invention may be used to manage, control and monitor job requests for a fleet of mobile robots comprising tens, hundreds or even thousands of individual autonomously-navigating robotic units. However, it should be understood that the "fleet" may also comprise a single autonomously-navigating mobile robot. Therefore, unless stated or otherwise dictated by context, the term "fleet of mobile robots," as used throughout this disclosure, should be construed as encompassing a fleet of any number of mobile robots, including a fleet of only one mobile robot. Autonomously-navigating mobile robotic units suitable for adaptation and use with embodiments of the present invention are manufactured and sold by Omron Adept Technologies, Inc., of San Ramon, Calif., USA.

In one aspect of the present invention, there is provided a job management system for processing job requests in a physical environment, such as a laboratory, manufacturing plant, order processing facility, distribution center, hospital or office building. In general, the job management system comprises a memory; a microprocessor coupled to the memory; a map (or map file) stored in the memory to define a floor plan corresponding to the physical environment; a queue manager that operates cooperatively with the microprocessor and the memory to select a mobile robot from the fleet and to determine an actual job location and/or an actual job operation associated with the request, all in accordance with the map, and a network interface device to transmit one or more commands to the selected mobile robot to make the selected robot carry out the job request. The map also defines a set of virtual job locations in respect to the floor plan, each virtual job location representing an actual job location in the physical environment, and also associates a set of virtual job operations with one or more of the virtual job locations in the set of virtual job locations, each virtual job operation representing an actual job operation in the physical environment. For example, the system operator may create and place a virtual job location on the floor plan called "battery charging station," which represents an actual battery charging station on the factory floor of the real world physical environment. The system operator may further create a virtual job operation, called "charge batteries," and associate the newly-created virtual job operation ("charge batteries") with the newly created virtual job location ("battery charging station"). Subsequently, copies of the map with the virtual job location and virtual job operation may be used by the mobile robots so that the mobile robots will automatically know that they should start executing the "charge batteries" job operation upon being sent or summoned to the "battery charging station" job location. It is to be understood that, depending on the situation, some virtual job locations may have no associated virtual job operations, while other virtual job locations may have one, dozens or even hundreds of associated virtual job operations.

When the queue manager on the job management system receives a job request, the job request may specify (1) a virtual job location without specifying a virtual job operation, (2) a virtual job operation without specifying a virtual job location, or (3) a virtual job location and a virtual job operation. If the request contains only a virtual job location, then the job management system of the present invention will use the map and the specified virtual job location to determine the actual job operation in the physical environment for the job request. Put another way, the map tells the job management system which virtual job operations, if any, are associated with the specified virtual job location. The map also tells the job management system (as well as the mobile robots) the actual job location in the physical environment. If the request contains only a virtual job operation, then the job management system of the present invention will use the map and the specified virtual job operation to determine the actual job location in the physical environment for the job request.

In preferred embodiments, the memory also contains a status profile and a configuration profile for each mobile robot. The status profile may comprise a file or data structure stored in the memory that includes records and/or fields suitable for holding and/or indicating one or more of a wide variety of different current status values or conditions for each mobile robot in the fleet, including without limitation the following: a robot identifier; a robot position; a robot heading; a current robot speed; a current job identifier; a current job status; a current job location; a proximity to the current job location; a current job destination path; an estimated time of arrival; an estimated time of departure; a robot idle time; a robot performance level; a robot security level; a robot battery charge level; a robot payload status; a robot payload error condition; a robot cargo status, and/or a robot cargo capacity. The configuration profile may comprise a file or data structure stored in the memory that includes records and/or fields suitable for holding and/or indicating one or more of a wide variety of different current configurations for each mobile robot in the fleet, including the following: a material handling capability; a material lifting capability; a material transporting capability; a manipulating capability; an object conveying capability; a measuring capability; a sensing capability; a pumping capability; a spraying capability; a vacuum capability; a drilling capability; a video recording capability; a sound recording capability; a sound producing capability; a navigation capability; a data input capability; a data output capability; a data communication capability; a printing capability; a displaying capability; a floor plan mapping capability; an energy absorption capability; an energy production capability; a maximum payload capability; a minimum payload capability; a maximum drive speed; a minimum drive speed; a maximum height; a minimum height; a location restriction; a zone restriction; a forbidden operation; a permitted operation; and/or a minimum clearance requirement.

Having determined the actual job location or the actual job operation for the job request, the job management system automatically selects a mobile robot from the fleet to handle the job request based on the status profiles and the configuration profiles stored in the memory. Thus, the queue manager determines, based on the data in the status profile or the configuration profile, for example, whether the selected mobile robot has a current status and a current configuration that is compatible with the job request. The queue manager further generates a command instruction which, when received by the selected mobile robot, will cause the selected mobile robot to automatically drive to the actual job location in accordance with floor plan defined by the map and/or to automatically perform the actual job operation.

As previously stated, the queue manager selects a mobile robot from the fleet to handle the job request based on whether the status profile, the configuration profile, or both the status profile and the configuration profile, indicate that the current status and/or the current configuration for the selected mobile robot is compatible with the job request. The current status may be judged "compatible" with the current job request, for example, if the status profile for the selected mobile robot shows that the current status of the selected mobile robot is "fully charged" and "not currently performing another assigned job request." On the other hand, the current status of the a mobile robot may be judged to be "incompatible" with the job request when the status profile indicates that the mobile robot's current cargo capacity is "none," and the job request requires picking up and transporting an item to another location. Similarly, in specific embodiments of the job management system, the queue manager could determine, based on the current configuration profile for the selected mobile robot, that the selected mobile robot has a current configuration that is compatible with the job request. The current configuration may be judged to be "compatible" with the job request when the configuration profile for the selected mobile robot indicates, for example, that the selected mobile robot has the proper equipment, the proper size and weight, and/or the proper characteristics and capabilities to handle both traveling to the actual job location and carrying out the job operation in the job request.

So, for example, if the job request received by the job management system includes a job location that requires traveling a very narrow and inclined corridor, and also includes a job operation that requires recording video and gripping and manipulating an object at the specified job location, then the queue manager would use the configuration profiles stored in the memory to ensure that the mobile robot selected to handle the job request is (a) equipped with a video camera, (b) equipped with a manipulator, (c) has suitably physical dimensions to fit through the narrow corridor, and (d) has sufficient locomotion, power, balance and stability characteristics to safely negotiate the slope of the inline in the corridor.

In some cases, two or more mobile robots in the fleet will have statuses and configurations that are compatible with the job location and job operation in the job request. In these situations, the queue manager may be configured to automatically determine, in accordance with an established status-based criteria, an established configuration-based criteria, or both, which one of the two or more compatible mobile robots in the fleet has a more favorable status and configuration for the job request. For example, a particular mobile robot may be judged to have a more favorable status and configuration than any of the other candidates because it is closer to the job location, capable of moving with a higher velocity, has a higher level of battery charge, makes less noise and/or has attached to it a higher resolution camera than any of the other mobile robot candidates.

In addition, in specific embodiments of the job management system, the queue manager could receive with the job request a specified time for performance of the job request. In this case, the queue manager may be configured to determine, based on the status profile for the selected mobile robot, whether the current status for the selected mobile robot is compatible with the specified time for performance. The current status may of the selected mobile robot may be determined to have a current status that is compatible with the specified time for performance because, for example, the selected mobile robot will be idle and not otherwise engaged at the specified time for performance. Similarly, the queue manager could determine, based on the configuration profile stored in the memory for the selected mobile robot, whether the current configuration for the selected mobile robot is compatible with the specified time for performance.

Further still, in specific embodiments of the job management system, the queue manager could receive a specified priority for the job request and determine, based on the status profile for the selected mobile robot, whether the current status for the selected mobile robot is compatible with the specified priority. Similarly, the queue manager could determine, based on the current configuration profile stored in memory for the selected mobile robot, whether the current configuration for the selected mobile robot is compatible with the specified priority. For example, a mobile robot in the fleet may be judged by the queue manager to have a current configuration that is "incompatible" with the specified priority because that mobile robot cannot travel through the physical environment at velocities dictated by the specified priority.

In specific embodiments of the job management system, the queue manager could receive a specified combination of job locations and job operations and determine, based on the status profile for the selected mobile robot, whether the current status for the selected mobile robot is compatible with the specified combination of job locations and job operations. Similarly, the queue manager could determine, based on the current configuration profile stored in memory for the selected mobile robot, whether the current configuration for the selected mobile robot is compatible with the specified combination of job locations and job operations.

Further still, in specific embodiments of the job management system, the queue manager could receive a specified route between job locations and determine, based on the status profile for the selected mobile robot, whether the current status for the selected mobile robot is compatible with the specified route. Alternatively, the queue manager could determine, based on the current configuration profile stored in memory for the selected mobile robot, whether the current configuration for the selected mobile robot is compatible with the specified route.

In specific embodiments of the job management system, the queue manager could receive a request to assign a particular mobile robot to handle the job request and determine, based on the status profile for the particular mobile robot, whether the current status for the particular mobile robot is compatible with the job request. In that regard, a different mobile robot could be selected for the job request automatically if the status profile for the particular mobile robot is not compatible with the job request. Similarly, the queue manager could determine, based on the current configuration profile stored in memory for the particular mobile robot, whether the current configuration for the particular mobile robot is compatible with the job request. In that regard, a different mobile robot could be selected for the job request automatically if the configuration profile for the particular mobile robot is not compatible with the job request.

In some embodiments of the job management system, the queue may also be configured to periodically receive status profile updates and/or configuration profile updates for the selected mobile robot, as well as for every mobile robot in the fleet. Further still, in specific embodiments of the job management system, the queue manager could receive a first planned path that the selected mobile robot plans to use to drive to the specified job location and a second planned path that a second mobile robot in the fleet plans to use. The queue manager then could make a determination as to whether the first planned path intersects the second planned path and, if select a different mobile robot to handle the job request.

In specific embodiments of the job management system, the queue manager could receive a signal indicating that no mobile robot in the fleet is available to handle the job request and, in that case, automatically delay selecting a mobile robot from the fleet to handle the job request until a mobile robot from the fleet becomes available. Additionally, in specific embodiments of the method, the queue manager could receive a signal indicating that the selected mobile robot failed to handle the job request and, in that case, automatically select a different mobile robot from the fleet to handle the job request based on the status profile and the configuration profile stored in the memory for the different mobile robot.

In another aspect of the present invention, a method for processing job requests on a job management system in a physical environment is provided. The first step in the method comprises the step of storing in a memory a map defining a floor plan for the physical environment, a virtual job location in respect to the floor plan, the virtual job location representing an actual job location in the physical environment, and associating one or more virtual job operations with the virtual job location, each virtual job operation representing an actual job operation in the physical environment. Next, the method stores in the memory a status profile and a configuration profile for each mobile robot in the fleet, and receives a job request by the queue manager, the job request comprising a specified job operation, a specified job location, or both. In the next step of the method, the queue manager automatically selects a mobile robot from the fleet to handle the received job request based on a status profile and a configuration profile stored in the memory for the selected mobile robot. And finally, in the last step, a network interface is used to automatically transmit over a command instruction to the selected mobile robot to cause the selected mobile robot to automatically drive to the actual job location in accordance with the floor plan, to automatically perform the actual job operation, or both drive to the actual job location and perform the actual job operation.

In still another aspect of the present invention, there is a provided a non-transitory computer-readable storage medium, such as a hard drive, flash memory device, CDROM or other memory-storage device, the storage medium having an executable program for processing job requests in a physical environment comprising a fleet of mobile robots. The executable program includes a collection of program instructions that, when executed by one or more microprocessors on a computer system, will cause the microprocessors to: (a) store in a memory device on the computer system a map that (i) defines a floor plan corresponding to the physical environment, (ii) defines a virtual job location in respect to the floor plan, the virtual job location representing an actual job location in the physical environment, and (iii) associates a virtual job operation with the virtual job location, the virtual job operation representing an actual job operation in the physical environment. The program instructions are further arranged to cause the computer system to receive a job request, the job request including the virtual job operation on the map, the virtual job location on the map, or both. Then the program instructions will cause the computer system: to automatically select a mobile robot from the fleet to handle the received job request; to automatically determine the actual job location based on the map and the virtual job operation if the job request does not include the virtual job location; to automatically determine the actual job operation based on the map and the virtual job location if the job request does not include the virtual job operation; and to transmit one or more commands from the computer system to the selected mobile robot to cause the selected mobile robot to (i) automatically drive to the actual job location represented by the virtual job location, (ii) automatically execute the actual job operation represented by the virtual job operation, or (iii) automatically carry out both steps of driving to the actual job location and performing the actual job operation.

BRIEF DESCRIPTION OF THE FIGURES

The accompanying drawings, which are incorporated in and constitute part of the specification, illustrate preferred embodiments of the invention, and, together with the description, serve to explain the principles of the present invention. In the drawings, like reference numbers indicate identical or functionally-similar elements.

FIG. 3 illustrates, by way of example, some of the data content of a map file defining a floor plan for the physical environment. The map file is stored in the memory of the mobile robot according to embodiments of the invention.

DETAILED DESCRIPTION OF EXEMPLARY EMBODIMENTS OF THE INVENTION

Figure 1:
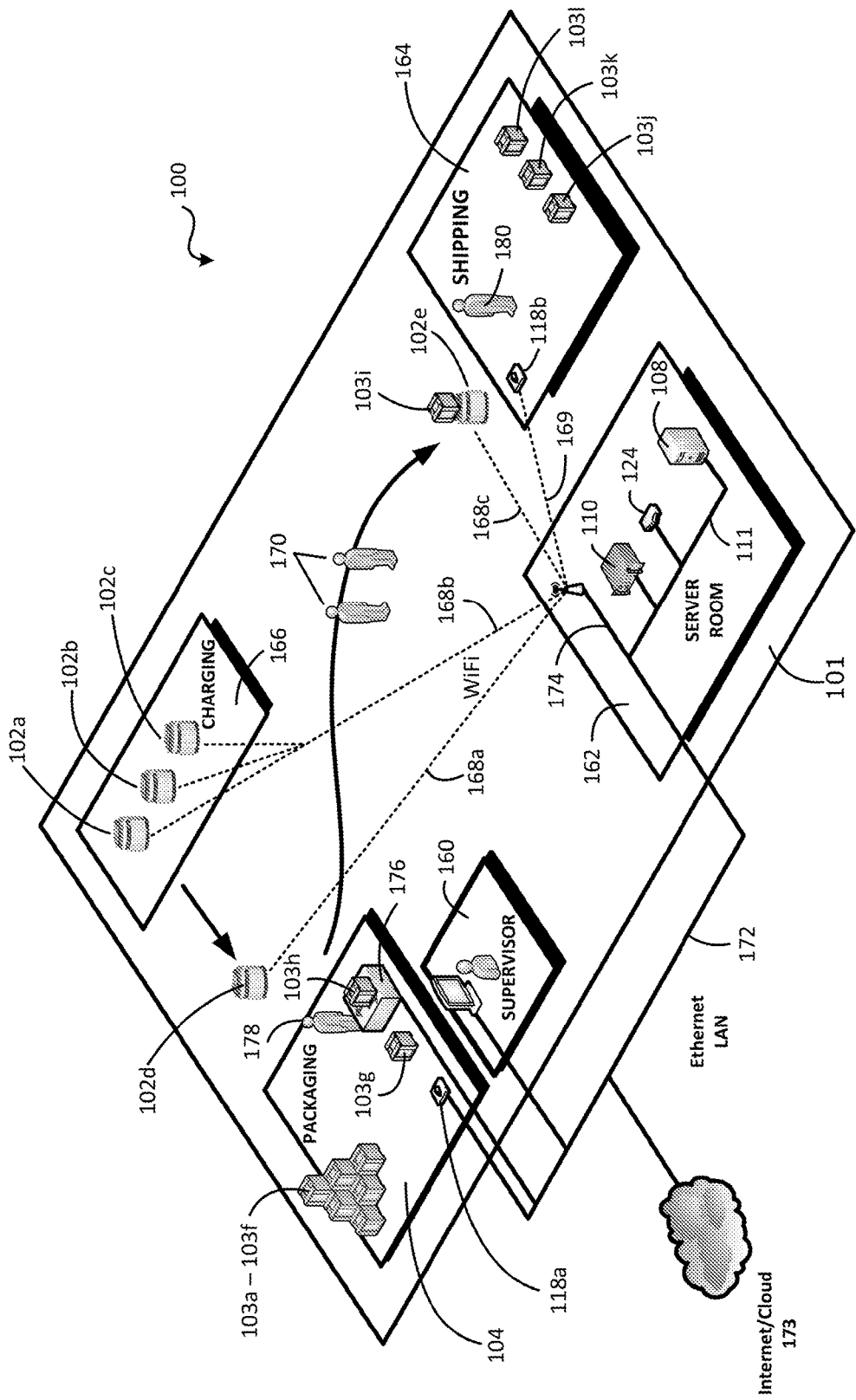
FIG. 1 shows a diagram illustrating an example of a physical environment in which a job management system of the present invention may be beneficially deployed to receive, manage, process and assign incoming job requests, where the physical environment includes a fleet of mobile robots for handling the incoming job requests.

Before explaining at least one embodiment of the present invention in detail, it is to be understood that the invention is not limited in its application to the details of the components and the arrangement of the components as set forth in the following description or illustrated in the drawings. The invention is capable of other embodiments and of being practiced and carried out in various ways. Also, it is to be understood that the phraseology and terminology employed herein are for the purpose of description and should not be regarded as limiting. For example, the discussion herein below generally relates to processing job requests associated with handling and transporting objects and material; however, it should be apparent that the inventive concepts described herein are also applicable to other applications and environments, including for example, industrial manufacturing.

As previously-stated, job management systems operating according to embodiments of the present invention are capable of receiving job requests from multiple sources, including without limitation:

Other automation systems sent directly to the queue manager;

Call buttons located throughout the facility;

Software-based calling devices, such as an application running on a desktop, laptop, or handheld device, located throughout the facility or at remote locations;

Input/Output devices mounted onboard each mobile robot (i.e. touchscreen, pushbuttons); and Mobile robots in the fleet.

The job management system prioritizes transportation requests, so that some requests can be handled sooner than others. The job management system is also configured to accept and queue a variety of incoming requests for the mobile robots in the fleet, including requests to have a mobile robot in the fleet:

Report to a single location

Report to a single location with a pre-determined drop off destination

Report to a single location with an unknown drop off destination, and have the drop off be instructed after arrival Report to a single location with an unknown drop off destination, and have multiple drop-offs be instructed after arrival Report to a single location with an unknown drop off destination, and have multiple drop-offs be instructed after arrival. While delivering, new destinations may be added to the robot's itinerary Run a random or defined route to look for items to pick up, and run through a series of drop-offs At any point and time, add additional destinations its itinerary Cancel a previously-assigned destination The queued job requests may be assigned to the mobile robots in an efficient fashion based on the current statuses and current configurations of the mobile robots. Statuses and configurations that may be used to determine suitability of a particular robot for a particular task may include, for example:

Proximity to pickup location

Battery charge-level on vehicle

Vehicle idle time

Estimated time of arrival (accounting for traffic)

Cargo capacity

Height and/or width of the mobile robot

Ability to traverse inclines

Obstacle avoidance capability

Gripping capability

Preferred embodiments of the job management system include an optimization module configured to optimize the handling of the queue to reduce response times and driving times. If a robot in the fleet is handling a pickup request, and a new request is received, but is not next-in-line, then embodiments of the present invention may elect to process the request out of order because a different robot is already near the pickup point. Compared to conventional factory transport systems, embodiments of the present invention provide a simplified structure and rule-set that is nevertheless capable of handling a wide variety of complex pickup, delivery and scheduling requests.

In some embodiments, a more simplified and efficient structure and handling may be achieved by using request processing modules that comply with the following rules or approaches. However, these rules and approaches are optional and not necessarily required in all embodiments.

All requests, whether sent directly to a mobile robot or sent directly to the queuing-manager are ultimately received by the queuing-manager. This permits the system to manage all requests in one location.

Pickup, drop-off, and route-based queue items may all be tracked in a single queue. This again makes it easier to manage and track transported items as well as robots.

Requests do not have to specify what type of mobile robot is required. This determination is made at time of assignment by the job management system, and uses the job operations that are associated with the job operation to determine what type of vehicle is needed. This approach simplifies the format of a queue requests and allows all requests to be in a common format.

In preferred embodiments, assignments of queued job requests are handled by a queue management routine that is independent of the working environment or industry. This permits easy modification and enhancement of the queue management routine without having to regression test every application-specific routines. The mobile robots in the fleet may be configured to receive commands and assignments from the job management system and send updates to the job management system via a variety of different data communication methods, protocols or standards, including but not limited to, 802.11, 802.15.4, broadband or LTE, to name a few.

In one example of a job management system operating in accordance with certain embodiments of the present invention, the job management system (which also may be referred to in some industries as an "warehouse management system" or "manufacturing execution system") is used to coordinate and manage job requests for jobs associated with transporting materials and equipment around a physical environment, such as a manufacturing, production, shipping or distribution facility. In this environment, mobile robots in the fleet may be configured to automatically pick up and deliver items, products, material, data or other cargo to various locations and/or workstations (which are sometimes referred to as "goals") in the facility, and may also be configured to engage with people and equipment, if needed, while servicing those locations and/or workstations. The mobile robots may engage and interact with people, for instance, through human-machine interface devices, such as display monitors, speakers, touchscreens, microphones, keyboards, buttons, printers, switches, voice recognition and voice command devices, attached to the mobile robots. The mobile robots may also be configured to engage and interact with equipment in the facility, such as machines, computers, workstations, automatic doors, elevators, conveyors, wireless transmitters and receivers, material carriers and encasements, through wireless communication interfaces, sensors, actuators and/or manipulators attached to the mobile robots.

FIG. 1 shows a diagram illustrating an example of a physical environment 100 in which a job management system 110 of the present invention may be beneficially deployed to receive, manage, process and assign incoming job requests associated with using a fleet of mobile robots 102a-102e to transport packaged items 103a-103l to various job locations in an enterprise, such as a manufacturing, production, shipping or distribution facility. In the depicted example, the physical environment 100 might be a factory floor 101, where finished products are packaged at a packaging station 104 (one example of a "job location" as that term is used in the context of this disclosure) and then transported to a shipping area 164 (another example of a job location) by mobile robots 102a-102e in the fleet. A multitude of other types of physical environments, or enterprises, including without limitation, order processing centers, manufacturing facilities, laboratories, hospitals, office buildings, educational facilities, etc., could also employ job management systems of the present invention to receive, manage and distribute job request to move items, data or materials.

As shown in FIG. 1, the physical environment 100 includes a factory floor 101 organized into a number of distinct job locations, including a packaging station 104, a supervisor workstation 160, a server room 162, a shipping area 164 and a charging area 166. The job management system 110 is located, in this case, in the server room 162, although it could be located elsewhere on the factory floor 101 or elsewhere in the physical environment 100. The job management system 110 could even be located outside the physical environment 100, such as in the Internet Cloud 173, so long as it is communicatively coupled to the Ethernet local area network (LAN) 172 in the physical environment 100 so that communication with the mobile robots 102a-102e, as well as other devices in the LAN 172 is enabled. In the example pictured in FIG. 1, the mobile robots 102a-102e are configured to transport packaged items 103a-103l between the various job locations on the factory floor 101 in response to high-level assignments and commands generated and transmitted to the mobile robots 102a-102e from the job management system 110. As shown in FIG. 1, the job management system 110 is configured to transmit the high-level commands to the mobile robots, and receive job requests and status reports back from the mobile robots 102a-102e, via an Ethernet local area network (LAN) 172 comprising TCP/IP connection 174 and Wi-Fi connections 168a-168c.

The job management system 110 includes a network interface device (not shown in FIG. 1) configured to receive the job requests from a job requesting system 108, which, in this example, is also located in the server room 162 and connected to the network interface device on the job management system 110 by a TCP/IP connection 111. The job requesting system 108 may comprise, for example, a warehouse management system ("WMS"), a manufacturing execution system ("MES"), an online or mail order processing system and/or an automated manufacturing system, as are well known in the art, or any other type of system or device capable of generating and submitting electronic job requests to the job management system 110. The job requesting system 108 may also include one or more less complex devices for generating job requests, such as a personal computer, a smart phone, an input/output device, a set of call buttons, or a human-machine interface. For example, a scale 176 located in the packaging station 104 could be electronically connected to the job management system 110 via Ethernet LAN 172 so that a mobile robot 102d in the fleet is automatically called to the packaging station 104 anytime the scale operator 178 weighs a packaged item 103h. The job management system 110 may also be configured to receive job requests from a plurality of Ethernet- and IEEE 802.11-based based call buttons 118a-118b located on the factory floor 101, which are communicatively connected to one or more network interface devices on the job management system 110 via the Ethernet LAN 172, TCP/IP connection 174 and Wi-Fi connection 169. Thus, a shipping clerk 180 working in the shipping area 164 may activate 802.11-based call button 118b to automatically send a job request to the job management system 110 to have a mobile robot 102e from the fleet autonomously drive itself to the shipping area 164. The call buttons 118a-118b may also be implemented using the IEEE 802.15.4 protocol, in which case the call button would communicate with the job management system 110 through a remote-I/O master station 124 on the network.

In preferred embodiments, the fleet of mobile robots 102a-102e comprises one or more of a variety of different (heterogeneous) types of autonomously-navigating mobile robots configured to automatically perform a variety of different jobs in the physical environment 100. Preferably, the mobile robots 102a-102e are capable of autonomously performing all of the navigation functions (e.g., localization and path planning) necessary for the mobile robots 102a-102e to automatically drive themselves from one job location to another job location on the factory floor 101 and automatically avoid colliding with stationary and/or non-stationary obstacles, including human factory floor workers 170, while doing so. The mobile robots 102a-102e may also be equipped with additional input/output devices, intelligence and equipment, such as onboard human-machine interfaces, RFID readers, environmental monitoring sensors, cameras and actuators, for engaging and interacting with equipment and human factory floor workers 170 and carrying out job requests received from the job management system 110. Examples of mobile robots suitable for use with the present invention are discussed and described in significantly more detail below with reference to FIGS. 5, 6 and 7.

Figure 2:
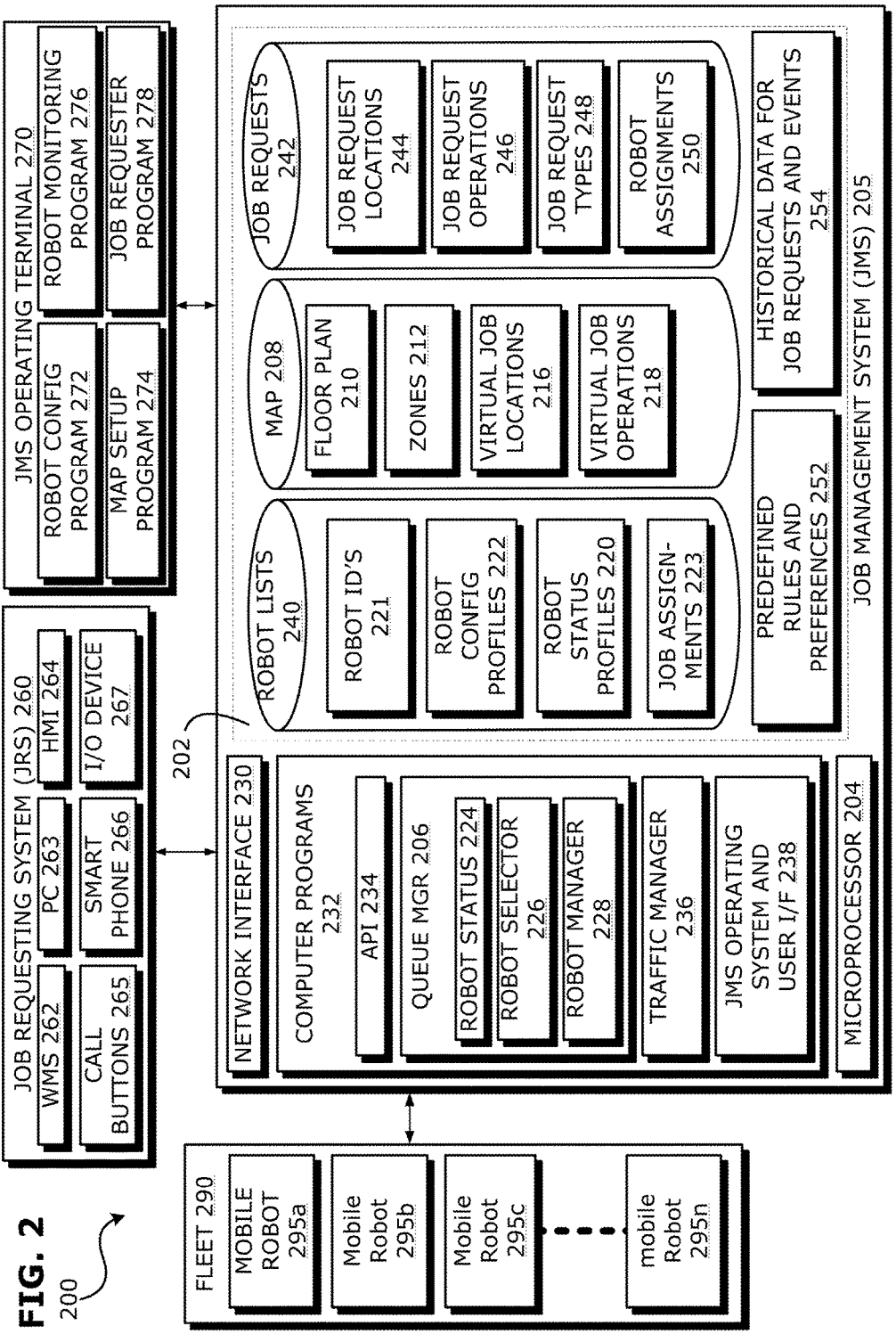
FIG. 2 shows a high-level block diagram illustrating the major functional components of a job management system configured to operate, in accordance with an exemplary embodiment of the present invention, within a factory automation system that includes a fleet of mobile robots.

FIG. 2 shows a high-level block diagram illustrating the major functional components of a factory automation system 200 and a job management system 205 configured to operate in accordance with an exemplary embodiment of the present invention. As shown in FIG. 2, the factory automation system 200 includes the job management system 205, which is communicatively coupled to a job requesting system 260, a JMS operating terminal 270 and a fleet 290 of autonomously-navigating mobile robots 295a-295n. The factory automation system 200 may also include a variety of other devices (not shown), such as personal computers, workstations, manufacturing and order processing tools, configured to communicate with the job management system 205 so as to facilitate automated processing and handling of mechanically- and electronically-generated job requests. As previously stated, the job management system 205 may be configured to communicate with the job requesting system 260 and the fleet 290 of autonomously-navigating mobile robots 295a-295n over a plurality of local area network connections, including without limitation TCP/IP, 802.11 and 802.15.4 connections.

The job requesting system 260 may include one or more devices for generating specific job requests and sending those job requests to the job management system 205. For example, the job requesting system 260 could include a warehouse management system ("WMS") 262 that generates and sends job requests to the job management system 205; one or more computers (e.g., personal computers or "PCs") 263; one or more call buttons 265, which may be located, for example, at users' desktops, at certain job locations, or attached to walls in the physical environment; one or more applications residing on various users' smart phones 266 or other mobile computing devices (e.g., laptop computers, tablet computers, dedicated portable job request units, etc.); human-machine interface ("HMI") devices 264 such as LCD-based touch-pad entry devices; and input/output ("I/O") devices 267 such as, for example, scanners, readers, sensors, etc. used in connection with automated processes. The WMS 262, personal computers 263, HMI 264, call buttons 265, smart phones 266 and I/O devices 267 may be located on the factory floor or elsewhere in the physical environment in which the job management system 205 of the present invention is configured to operate, so long as the devices are communicatively coupled to the job management system 205 via links and connections in the factory automation system 200.

Additionally, the factory automation system 200 suitably includes one or more JMS operating terminals 270 configured to communicate with the job management system 205. This operating terminal 270 executes a variety of configuration and setup programs, by means of which a supervisor or other human operator can establish, modify and manage maps, lists, rules and preferences on the job management system 205, generate new job requests for the job management system 205, as well as monitor the progress and statuses of the fleet 290 of mobile robots 295a-295n as job operations associated with the job requests are carried out. Thus, the JMS operating terminal 270 preferably includes at least a robot configuration program 272 for establishing and managing robot configurations, a map setup program 274 for creating and/or modifying the map 208 (described in more detail below), a robot monitoring program 276 by which the operator can "watch" robots as they move about the factory floor, and a job requesting program 278 by which the operator can create new job requests. In preferred embodiments, the JMS operating terminal 270 uses PC-executable computer programs, such as MobilePlanner™, available from Adept Technologies, Inc., of Pleasanton, Calif., USA, to create maps and floor plans, to define and establish job locations, job operations, zones and sectors on the map 208, and to establish robot physical characteristics, capabilities and restrictions in the robot configuration profiles 222. After the initial setup is complete, another computer program, such as MobileEyes™, also available from Adept Technologies, Inc., of Pleasanton, Calif., USA, can be used to monitor where all of the mobile robots 295a-295n are located during operation.

Generally speaking, job management system 205 comprises a memory 202, a microprocessor 204 coupled to the memory 202 and a queue manager 206 that operates cooperatively with the microprocessor 204 and the memory 202 to receive and process job requests by intelligently selecting and assigning mobile robots from the fleet 290 to carry out job operations in response to the received job requests. The job management system 205 also includes various computer programs 232 or software modules; various lists of rules and preferences 252 and one or more data storage devices (or databases), stored in the memory 202, which contains data and information—described in greater detail below—that is used by the queue manager 206 to coordinate and monitor the operation of the various mobile robots 295a-295n in the factory automation system 200. Additionally, the job management system 205 includes a network interface device 230, such as a wired or wireless Ethernet adapter, which provides connectivity with various other components in the factory automation system 200. As will be recognized by those having skill in the art, job management system 205 may be implemented using any general purpose, programmable digital computing device including, for example, a personal computer, a programmable logic controller, a distributed control system, or other computing device. The computer system can include a central processing unit (CPU) or microprocessor, random access memory (RAM), non-volatile secondary storage (e.g., a hard drive, or flash memory device), and various types of network interface devices (e.g., wired or wireless Ethernet cards and digital and/or analog input/output cards). Program code and instructions from the computer programs 232 and data from the non-volatile secondary storage comprising the memory 202 may be loaded into the RAM and provided to the microprocessor 204 for execution. The computer programs 232 can generate results for display, output, transmission, or storage. The computer programs 232, which may comprise one or more software modules, contain computer-executable instructions that cause the microprocessor 204 to perform a variety of specific tasks required to receive various job requests, coordinate execution of the various jobs requested, and dispatch mobile robots 295a-295n to carry out the job operations associated with the various job locations and job requests. The computer programs 232, microprocessor 204 and memory 202 are flexible, and may be configured to use a large variety of different predefined rules and preferences 252 established by a system operator via the JMS operating terminal 270.

The computer programs 232 on the job management system 205 include an application programming interface (API) 234, which is, in essence, a "library" of function calls and subroutines that permit the various other software programs or modules in the factory automation system 200 to communicate with each other. Another computer program 232 operating on the job management system 205 is the queue manager 206, which selects particular mobile robots from the fleet 290 to carry out job requests, as will be described in significantly greater detail below. To this end, the queue manager 206 comprises a robot status manager 224 (i.e., a collection or module of computer-executable program instructions) that monitor the current statuses of the mobile robots in the fleet 290, a robot selector 226 that selects the appropriate mobile robot to handle the job request based on the job request, the configurations and statuses of the mobile robots 295a-295n in the fleet 290, and a robot manager 228 that transmits command signals to the fleet 290 of mobile robots 295a-295n via the network interface 230 to cause the selected mobile robots to drive to the physical locations associated with the virtual job locations in the received job requests and/or carry out physical job operations associated with the virtual job operations in the received job requests.

Preferably, the computer programs 232 executing on the job management system 205 also include a traffic manager module 236, which helps control traffic flow within the physical environment so as to avoid, if possible, a situation where too many mobile robots 295a-295n are trying to move through the same area in the physical environment, thereby increasing the potential for mobile robot "traffic jams." The traffic manger module 236 does not plot the travel routes for the mobile robots 295a-295n. Rather, it typically obtains sufficient information about the current status, current heading and planned routes from each mobile robot in the fleet 290 of mobile robots 295a-295n, and broadcasts this information over the wired and wireless communications links using the network interface 230 so as to permit all of the mobile robots 295a-295n to "know" where other mobile robots in the fleet 290 are headed. Armed with this information, each mobile robot 295a-295n in the fleet 290 is then able plot its own path to its intended job location so as to avoid coming near or into contact with other mobile robots in the fleet 290, thereby avoiding potential traffic jams.

The traffic manager module 236 is also configured to use this path broadcasting to help mobile robots 295a-295n operate in tight spaces together. Although it does not actually plan paths or routes through the physical environment for the mobile robots, the traffic manager module 236 on the job management system 205 can be configured to make determinations about which mobile robots will have a relatively higher priority while attempting to traverse the same physical areas in the physical environment simultaneously. For example, if two robots happen to be travelling in the same direction in a tight space, one behind the other, and the mobile robot in the rear happens to be carrying out a job request that has a higher priority than the job request being carried out by the mobile robot in the lead, then the traffic manager module 236 preferably includes program instructions arranged to send a command instruction to the leading mobile robot that causes the leading mobile robot to slow down or come to a stop so that the mobile robot in the rear can pass. On the other hand, if it is important that the mobile robot in the lead not be delayed, then the traffic manager module 236 may be configured lower the priority of the mobile robot in the rear position, or raise the priority of the mobile robot in the leading position, so that the mobile robot in the rear position does not attempt to leapfrog the mobile robot in the lead position.

The memory 202 includes one or more tables, lists and/or databases used by the job management system 205 to track job requests, mobile robots and job assignments delegated to the mobile robots. These tables, lists and databases may comprise, for example, a robot lists database 240, a map database 208 and a job requests database 242. The robot lists database 240 includes identification records 221, robot configuration profiles 222, robot status profiles 220 and current job assignments 223 for each mobile robot 295a-295n in the fleet 290.

The mobile robots 295a-295n in the fleet 290 may have different physical characteristics, including, for example, being equipped with a variety of different actuators, conveyor belts, handlers, manipulators, support platforms, payload carriers, trailers or totes. The robot configuration profiles 222 track the current physical characteristics for every mobile robot in the fleet 290, including for example, any equipment attached to the mobile robot, as well as any restrictions or capabilities associated with the mobile robot or the attached equipment. Thus, the robot configuration profile 222 for a given robot may be configured to track, for instance, whether the robot, as currently configured and equipped, is capable of material handling, material lifting, material transporting, manipulation, conveying, measuring, sensing, pumping, spraying, vacuuming, drilling, video recording, sound recording, sound producing, navigation, data input, data output, data communication, printing, displaying, floor plan mapping, energy absorption or energy production. The robot configuration profile 222 may also be used to keep track certain constraints or restrictions associated with a mobile robot in the fleet, such as a maximum payload, a minimum payload, a maximum drive speed, a minimum drive speed, a maximum height, a minimum height, a location restriction, a zone restriction, a forbidden operation, a permitted operation, and/or a minimum clearance requirement. In preferred embodiments, the queue manager 206 on the job management system 205 comprises program instructions executable on the microprocessor 204 that, when executed by the microprocessor 204, cause the microprocessor to select a mobile robot from the fleet 290 to handle each job request based at least in part on whether the information stored in the robot configuration profiles 222 indicate that the selected mobile robot has the proper equipment and/or configuration for handling the job request.

The robot status profiles 220 track the current statuses for the mobile robots 295a-295n in the fleet 290 such that when a job is assigned to a selected mobile robot, the selected mobile robot is able to remain in contact with the job management system 205, via the network interface device 230 and API 234, so that the mobile robot is able to provide the job management system 205 with status updates on the progress and completion of that job. For example, if some cargo is loaded onto the mobile robot, then the mobile robot is able to transmit a status update to the job management system 205 indicating that the mobile robot's cargo hold is loaded with cargo. This status update would be stored in the robot status profile 220 for the mobile robot, and used by the queue manager 206, if necessary, to prevent the queue manager 206 from assigning another job to the mobile robot that requires that the mobile robot have an empty cargo hold. When the mobile robot completes the job by unloading the cargo hold, it sends another status update to the job management system 205 to be stored in the mobile robot's status profile 220, where it can be relied upon by the queue manager 206 when the queue manager 206 needs to select another mobile robot to handle another incoming job request. In addition to the status of the cargo hold for each mobile robot, the robot status profile 220 in the robot lists database 240 can be used to track and provide up-to-date status information about many other important states associated with the mobile robot, including for example, the mobile robot's identification number, position, heading, current speed, current job, current job status, current job location, proximity to the current job location, current job destination path, estimated time of arrival, estimated time of departure, estimated time of job completion, length of time in an idle state, performance level, security level, battery charge level, payload status, payload error condition and remaining cargo capacity. In preferred embodiments, the queue manager 206 on the job management system 205 comprises program instructions executable on the microprocessor 204 that, when executed by the microprocessor 204, cause the microprocessor to select a mobile robot from the fleet 290 to handle each job request based at least in part on whether the information stored in the robot status profiles 220 indicate that the current status of the selected mobile robot is compatible with the job request.

The job requests database 242 tracks information about the current job requests, including, for instance, current job request locations 244, current job request operations 246, current job request types 248 and current robot assignments 250 for each job request. Thus, the job requests database 242 identifies all of the various job requests that have been received, e.g., via a job request code number, and it tracks the current status of each of those jobs. Status information for each job request could include, for example, whether a given job request has been assigned to a mobile robot, and if so, the robot to which it has been assigned; what the sub-status of the job is; etc. As for the job status or sub-status, it could include states such as "pending," meaning the job request has not yet been assigned to a robot; "in progress," meaning the job request has been assigned to a robot and the robot is executing it; etc. Furthermore, depending on the nature of the job request—for example, if a robot simply needs to transport an item to a given location for someone to use the item or if the robot actually needs to perform some further task (such as drilling or cutting)—the status might include more specific sub-state identifiers such as "en route" or "travelling;" "arrived;" "performing function;" or "completed. Job request types 248 information may include, for example, whether the job request is a "pickup" request, a "drop off" request, or "pickup and drop off" request. Thus, as the job management system 205 receives the various job requests from the job requesting system 260, the job requests are added to the job request database 242, and as the job requests get assigned to various robots, records in the job requests database 242 and robot lists database 240 are used to track this information. It may also be desirable to record in the memory historical data for job requests and events 254, such as when a job request was received, when it was assigned to a particular mobile robot, and when the job request was completed, in order to evaluate operation of and troubleshoot the system.

Figure 4:
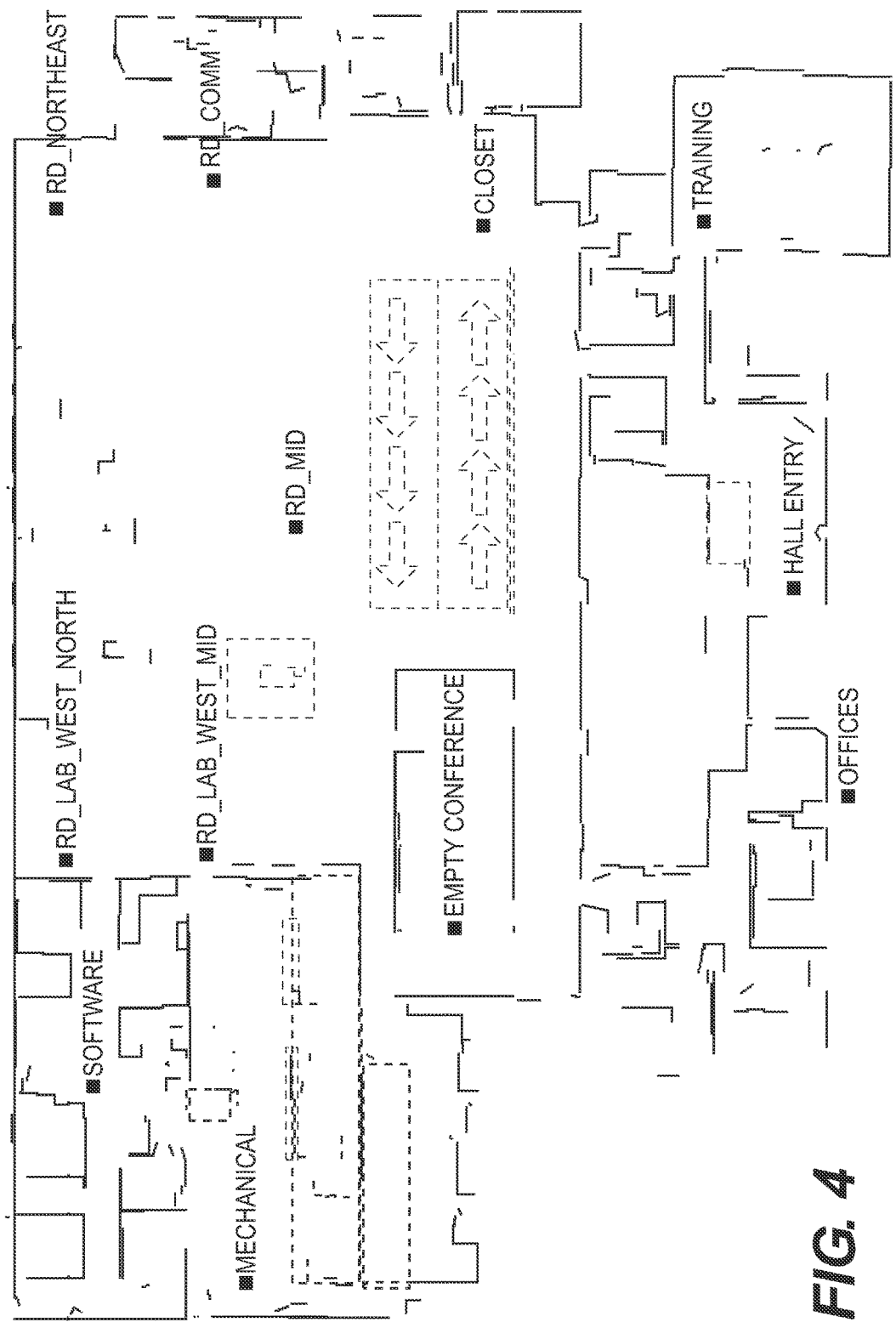
FIG. 4 shows a graphical representation of the map file illustrated in FIG. 3.

Map 208 stored in the memory 202 defines a floor plan 210 for the physical environment. The map 208 may be created and stored in the memory 202 by the queue manager 206, by another application program running on the job management system 205, or a map setup program 274 that may be invoked and executed, for instance, on the JMS operating terminal 270 by a human operator. FIG. 3 shows an example of the data content for a computer file comprising the map 208. FIG. 4 shows a graphical representation of the map 208. In preferred embodiments, the map 208 also defines a collection of operator-configurable zones 212 in the physical environment, which may be used to control where the mobile robots 295a-295n in the fleet 290 can and cannot go in the physical environment represented by the floor plan 210, and optionally impose certain operating constraints on those mobile robots. For example, map 208 could define a "FORBIDDEN" zone on a section of the floor plan 210 that will cause an automatic navigation system executing onboard the mobile robots to always plot a course around that zone rather than traverse it. Similarly, the map 208 might include a "ONE WAY" zone for a portion of the floor plan 210 that causes the mobile robots' onboard navigation systems to always travel through that zone in the same direction. The map 208 may also include coordinate information about other stationary obstacles that should be avoided by the mobile robots, such as furniture and machinery.

In preferred embodiments, the map 208 also defines a set of one or more virtual job locations 216 in respect to the floor plan 210, each virtual job location representing an actual job location in the physical environment. For at least some of the virtual job locations 216 on the floor plan 210, the map 208 also defines a set of one or more virtual job operations 218 to be performed automatically at that virtual job location, each virtual job operation representing an actual job operation to be performed in the physical environment. The job locations and job operations in the map are referred to as "virtual" job locations and "virtual" job operations because they are defined in terms of the map 208 and floor plan 210, which themselves are abstract representations of the actual physical environment. It is understood, however, that the mobile robots 295a-295n drive navigate and find their intended destinations in the physical environment by reference to the map 208 and the floor plan 210. Thus, a virtual job location may be thought of as a named "place," on the map's defined floor plan, which represents a corresponding named "place," in the physical environment represented by the map's floor plan. Likewise, a virtual job operation may be thought of as named operation in the map data, which represents a corresponding named operation in the real-world of the physical environment, which named operation can be performed by one or more of the mobile robots 295a-295n in the fleet 290. The map 208 may contain, for example, data defining where a particular job location exists in terms of coordinates delineating the floor plan 210, as well as certain job operations 218 that should be carried out automatically upon arrival at that particular job location.

In response to receiving a job assignment from the job management system 205, the onboard navigation systems on the mobile robots 295a-295n may be configured to use a copy of the map 208, a copy of the floor plan 210 and the coordinates in the floor plan 210 to drive the mobile robot to a set of coordinates on the floor plan 210, as defined by the map 208, thereby causing the mobile robot to drive itself to an actual job location in the real-world of the physical environment. So, for example, if the map 208 defines a virtual job location called "packaging area," which represents a real packaging area in the real world of the physical environment where packaging takes place, and the map 208 also identifies, in terms of floor plan coordinates, where on the floor plan 210 the "packaging area" is located, then the onboard navigation systems on the fleet 290 of mobile robots 295a-295n are configured to use copies of the map 208, copies of the floor plan 210 and the coordinates to automatically and autonomously drive themselves to the real-world actual packaging area represented by the virtual packaging area defined by the map 208.

In another example, the job management system 205 may send a command signal to a mobile robot in the fleet 290 to make the mobile robot perform a certain defined (virtual) job operation, such as "Load Merchandise," without identifying, in the command signal itself, any particular virtual job location where the "Load Merchandise" job operation should be performed. But the map 208 may has an entry for the "Load Merchandise" operation, which associates the "Load Merchandise" operation with a virtual job location on the map 208, job location may be called, for example, "Merchandise Storage." Copies of the map 208, and all of its virtual job locations and associated virtual job operations, are downloaded to the memories of the mobile robots 295a-295n. As a result, the association between the "Load Merchandise" job operation and the "Merchandise Storage" job location becomes known to the mobile robots 295a-295n. Knowing about the association permits the onboard navigation systems in the mobile robots 295a-295n to derive the actual job location(s) for carrying out the command to perform the "Load Merchandise" operation.

Similarly, if the job management system 205 sends a command to a mobile robot in the fleet 290 to perform the operation "Charge Battery," the onboard navigation system on the mobile robot will use a copy of the map 208 to obtain the current locations of battery charging stations in respect to the floor plan 210, as well as the current availability of the nearby battery charging stations, and based on this information, automatically drive the mobile robot to the nearest battery charging station that is not currently being used by another mobile robot.

The map 208 may also dictate through its definitions that certain virtual job operations 218 shall occur at certain virtual job locations 216. In this case, when the job management system 205 sends a command to a mobile robot in the fleet 290 instructing the mobile robot to go to a particular location on the floor plan 210, the command instruction does not necessarily need to specify which job operations the mobile robot should carry out upon arrival because the map 208 in the mobile robot's memory 202 has already associated one or more job operations 218 with that particular job location. So, if the job management system 205 sends a command instruction to a mobile robot in the fleet 290 that specifies a virtual job location, such as "Go To Battery Charging Station No. 5," without specifying a virtual job operation to perform upon arrival at the specified virtual job location, the mobile robot may be configured to automatically start charging its battery on arrival because the definitions and attributes stored in the map 208 indicate that battery charging is one of the job operations associated with battery charging station No. 5.

Thus, using the map's defined floor plan 210, as well as the job location 216 and job operations 218 in the map 208, job management systems of the present invention are capable of generating and sending to mobile robots 295a-295n in the fleet 290: (a) job requests that specify job locations without specifying job operations, (b) job assignments that specify job operations without specifying job locations, and (c) job assignments that specify both job locations and job operations.

The memory 202 also holds robot status profiles 220 and robot configuration profiles 222 for each mobile robot 295a-295n in the fleet 290. Typically, although not necessarily, the robot configuration profiles 222 will be established on the job management system 205 by a system operator interacting with a robot configuration program 272 executed on the JMS operating terminal 270. When the job management system 205 receives a job request that includes a specified job operation and/or a specified job location, the queue manager 206 automatically selects a mobile robot 295a-295n from the fleet 290 to handle the job request based on the robot status profiles 220 and the robot configuration profiles 222 stored in the memory 202. Thus, the queue manager 206 determines, based on the data in the robot status profile 220 or the robot configuration profile 222, for example, whether the selected mobile robot has a current status and a current configuration that is compatible with the received job request. The queue manager 206 further generates a command instruction which, when received by the selected mobile robot in the fleet 290, will cause the selected mobile robot to automatically drive to the specified job location in accordance with floor plan 210 defined by the map 208 and/or to automatically perform the specified job operation in accordance with the job operations 218 stored in the map 208.

As previously stated, the queue manager 206 includes program instructions for a robot selector 226, a robot manager 228 and a robot status 224, which are together responsible for processing the job requests currently being tracked in the job requests database 242 and assigning those job requests to the appropriate mobile robots 295a-295n in the fleet 290. That selection process can be done based on a number of different factors and/or preferences, including the current statuses and current configurations of the mobile robots 295a-295n in the fleet 290. So, for example, if the job request requires a mobile robot that has a conveyor belt or a manipulator on top, then the robot selector 226 and robot manager 228 in the queue manager 206 will, in accordance with information obtained from the robot configuration profiles 222, only select and assign a mobile robot that has a conveyor belt or manipulator. If the job request also requires that the selected mobile robot operate continuously for a long period of time, or travel a relatively large distance to carry out the job request, then the robot selector 226, robot manager 228 and robot status manager 224 in the queue manager 206 will, in accordance with information obtained from the robot status profiles 220, only select and assign a mobile robot that has a sufficient battery charge to carry out the job, thereby avoiding selection of a mobile robot that might not be able to complete the job without stopping for a battery charge.

The order of processing of job requests by the modules in the queue manager 206 may be optimized in accordance with the particular application where the job management system 205 is being used and/or in accordance with operator preference. For example, job requests could be handled on a first-in-first-out (FIFO) basis, such that every job request is handled according to the order in which they are received. However, other processing schemes could be used, whereby job requests are processed in a different order. If, for example, the next job request to arrive in the queue requires that a mobile robot be sent to a very distant destination in the physical environment in order to pick up an item, then the queue manager 206 may be configured to productively and efficiently assign mobile robots to handle subsequently-arriving job requests first, because doing so will permit a single mobile robot to deliver other items to nearby destinations while the mobile robot is in route to the very distant destination, thus permitting a single mobile robot to handle multiple job requests at once. This type of job request handling optimization typically resides in the robot selector 226 and robot manager 228 modules of the queue manager 206. Preferably, the queue manager 206 is also configured to be able to reassign a mobile robot that is in the middle of carrying out a job request, based on a determination by the robot selector 226 and robot status manager 224 modules that it may be best to have a different mobile robot service the previously-assigned job request.

Figure 5:
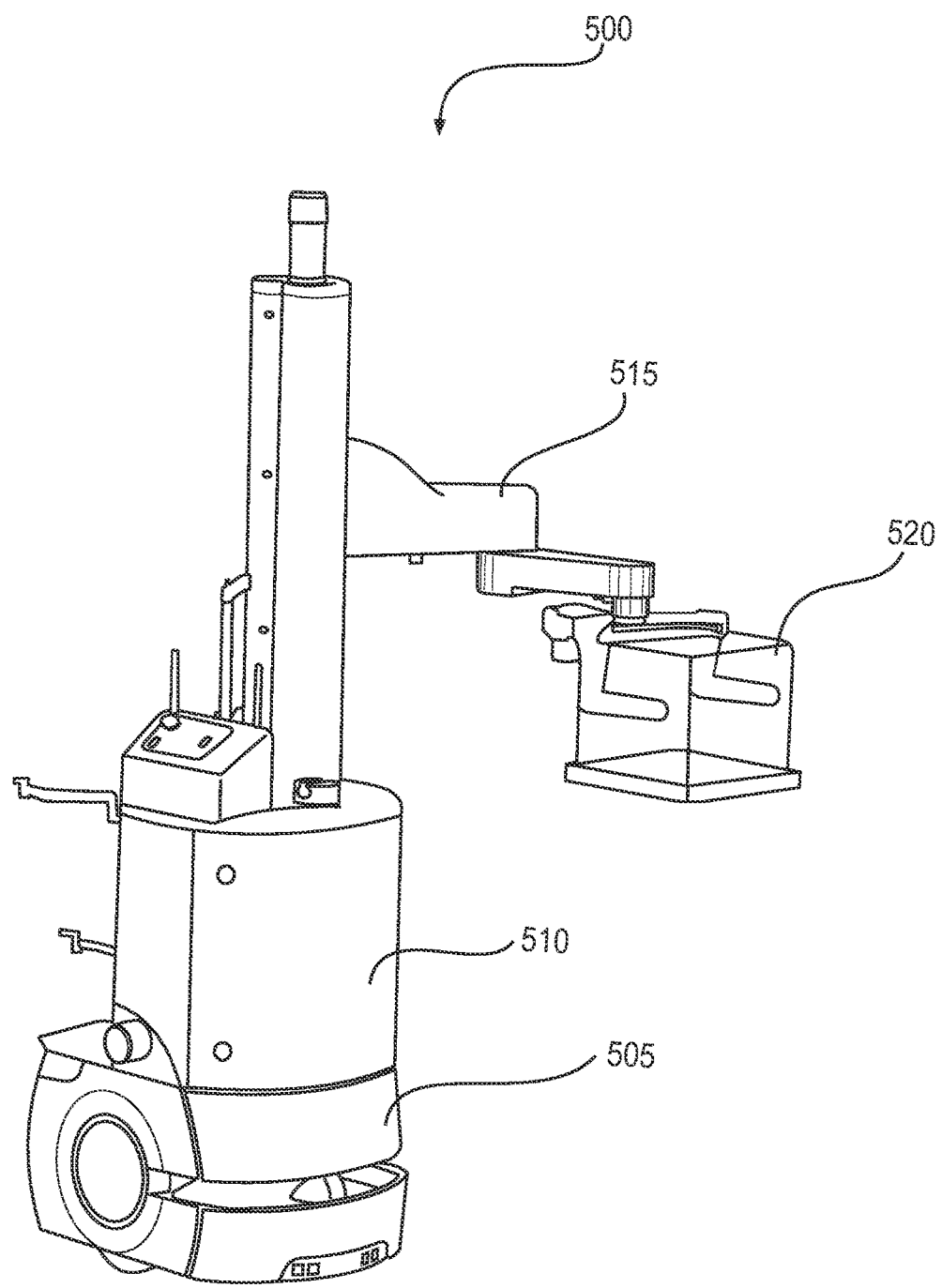
FIGS. 5 and 6 show exemplary embodiments of mobile robots configured to operate in accordance with the present invention FIG. 7 contains a high-level block diagram illustrating, by way of non-limiting example, some of the primary physical and logical components in an exemplary mobile robot configured to operate according to embodiments of the present invention.
Figure 6:
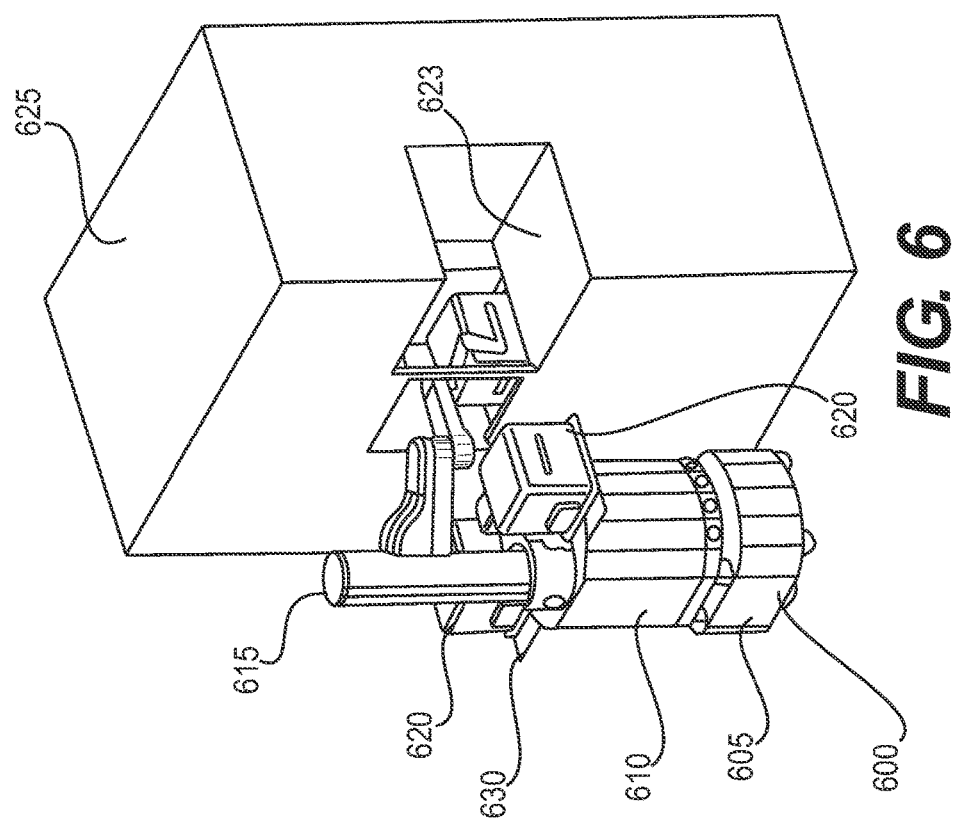

FIGS. 5 and 6 show examples of autonomously-navigating mobile robots suitable for use in the fleet 290 of mobile robots 295a-295n managed and controlled by the job management system 205 in accordance with the present invention. As shown best in FIG. 5, an embodiment of the mobile robot 500 includes a robot base 505 configured to carry a robot payload 510. In this example, the robot payload 510 includes an articulated mechanical arm actuator 515 configured to identify, grasp and lift standard manufacturing interface "SMIF" pods 520 used in semiconductor wafer fabrication and cleanroom environments. As shown in FIG. 6, mobile robot 600 also comprises a robot payload 610 having an articulated mechanical arm actuator 615. The articulated mechanical arm actuator 615 is configured to remove SMIF pods 620 from a platform 623 on workstation 625 and place the SMIF pods 620 on supports 630 attached to the robot payload 610. In preferred embodiments, the articulated mechanical arm actuator 615 may comprise a 4-degree of freedom SCARA (Selectively Compliant Articulated Robot Arm) or 6-degree of freedom articulated arm that is mounted on the robot base 605 of the mobile robot 600.

The robot base controller in the robot base 605 is programmed to activate the onboard navigation system in the robot base 605 to so that the mobile robot 600 carries the SMIF pods 620 directly to another location or workstation without following markers, rails or wires, and without colliding into stationary or non-stationary obstacles. More particularly, the onboard navigation system in the robot base 605 automatically determines, in accordance with a map stored on the robot base 600, a path to the next workstation. The onboard navigation system then uses the path to drive the mobile robot 600 to the location of the next workstation, avoiding negative and positive obstacles, as well as other robotic transporters, along the way.

Figure 7:
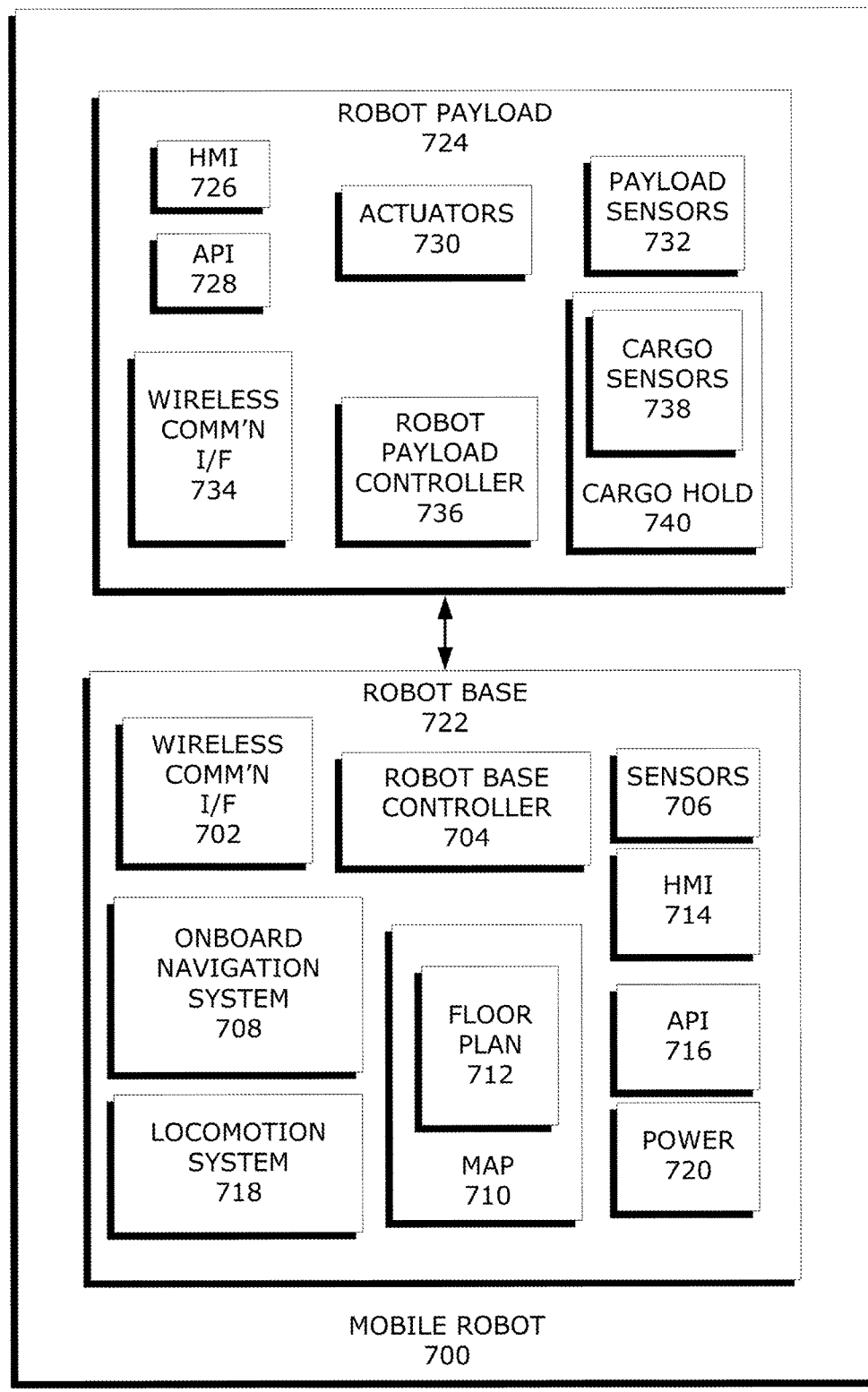

FIG. 7 contains a high-level block diagram illustrating, by way of non-limiting example, some of the primary physical and logical components in an exemplary mobile robot 700 configured to operate according to embodiments of the present invention. As shown in the block diagram of FIG. 7, the exemplary mobile robot 700 includes a robot base 722 and a robot payload 724. The robot base 722 comprises a variety of hardware and software components, including a robot base controller 704, an onboard navigation system 708, a locomotion system 718, a map 710 defining a floor plan 712, a wireless communication interface 702, sensors 706, a human-machine interface 714, an application programming interface (API) 716 and a power system 720.

The robot base controller 704 comprises computer program instructions executable on a microprocessor (not shown) on board the robot base 722 to initiate, coordinate and manage all of the automation functions associated with the mobile robot 700, including without limitation, handling of job assignments, automatic locomotion and navigation, communications with other computers and other robots, activating the robot payload functions and controlling power functions. The robot base controller 704 has an assignment manager (not shown) that keeps track of all of the robot's assignments and job operations. When a job assignment is received by the mobile robot 700, the robot base controller 704 activates the other subsystems in the mobile robot 700 to respond to the job assignment. Thus, the robot base controller 704 generates and distributes the appropriate command signals that cause other processing modules and units on the mobile robot 700 to start carrying out the requested job. So, for example, when the mobile robot 700 receives a job assignment from the job management system that requires that the mobile robot 700 drive itself to a certain location in the physical environment, it is the robot base controller 704 that generates the command signal that causes the onboard navigation system 708 to start driving the mobile robot 700 to the specified destination. The robot base controller 704 also provides an activation signal for the robot payload 724, if necessary, to cause the robot payload 724 to perform a particular operation at the specified job location. The robot base controller 704 also manages and updates the map 710, and the floor plan 712, when appropriate, based on updated map or floor plan information received from other computer systems or other robots in the computer network. The robot base controller 704 also receives assignment status information, if any, from the robot payload 724 and, if appropriate, relays the status information out to a remote job management system (not shown), which typically delegates job assignments to the mobile robot 700. Typically, the robot base controller 704 will communicate with the job management system via an application programming interface (API) 716 and a wireless communications interface 702.

The mobile robot 700 also includes a map 710 that defines a floor plan 712 corresponding to the physical environment, and also defines a set of job locations in terms of the floor plan 712. The map 710 also associates one or more job operations with one or more of the job locations in the set of job locations. Thus, the map 710 on the mobile robot 700 is substantially a copy of the map 208 on the job management system 205. FIG. 3 shows an example of the data content for a computer file comprising the map 710. FIG. 4 shows a graphical representation of the map 710. Each job location on the floor plan 712 corresponds to an actual location in the physical environment. Some of the job locations on the floor plan 712 will also have associated with them a set of one or more job operations to be carried out automatically by the mobile robot 700 after the mobile robot 700 arrives at the actual location. The map 710 may be obtained by the robot base controller 704 from the remote job management system (not shown) or, alternatively, from another mobile robot or from a standalone operating terminal for the network (not shown). Certain job operations on the floor plan 710 may have multiple locations in the physical environment. It is understood, however, that not all job operations need to be pre-programmed into the map 710. It is also possible for job operations to be commanded as needed by the robot base controller 704, or the remote job management system, irrespective of the whether or not the job operation is defined in the map 710.

The onboard navigation system 708, operating under the control of the robot base controller 704, handles all of the localization, path planning, path following and obstacle avoidance functions for the mobile robot 700. If the system includes a positive and negative obstacle avoidance engine to help the mobile robot 700 avoid colliding with objects that may be resting on the floor but who's shape is not appropriately identified by the mobile robot's horizontally scanning laser, and to avoid driving into gaps in the floor, this functionality is encompassed by the onboard navigation system 708. The onboard navigation system 708 automatically determines the job location for the job assignment based on the map and the job assignment. Using sensors 706, the onboard navigation system 708 also detects when driving the mobile robot along a selected path from the mobile robot's current position to an actual location in the physical environment will cause the mobile robot to touch, collide or otherwise come too close to one or more of the stationary or non-stationary obstacles in the physical environment. When the onboard navigation system 708 determines that contact with an obstacle might occur, it is able to automatically plan a second path to the intended job location, in accordance with the map, to avoid the contact. The path planning may be accomplished using any one of a variety of robot path planning techniques known in the art. One such path planning technique is discussed in detail in Chapter 7 of the book "Artificial Intelligence and Mobile Robots," First Edition, published in 1998 by AAAI Press, and edited by David Kortenkamp, R. Peter Bonnaso and Robin Murphy. For purposes of the present invention, the path planning engine plans a path that avoids all of the locations that have been identified as containing obstacles. The onboard navigation system 708 may also use sensing lasers to sample objects in the physical environment, and compare the samples with information in the map 710. This process is called "laser localization," or "Monte Carlo localization with a laser." Another known technique, called light localization (described in U.S. Pat. No. 7,650,013 issued to Dietsch et al.), involves using a camera to find lights in the ceiling and then comparing the lights found to lights identified on the map 710. All of these different techniques may be employed to help the onboard navigation system 708 determine its current position relative to the job location.

After the onboard navigation system 708 determines an alternative second path to the floor plan location representing the actual job location, it operates in combination with the locomotion system 718 to drive the mobile robot 700 from its current location to the actual job location using the second path. In some embodiments, the onboard navigation system 708 may subsequently determine that driving the mobile robot 700 to the actual job location along the second path may cause the mobile robot 700 to come into contact with another stationary or non-stationary obstacle, in which case the onboard navigation system 708 creates and uses a third path, in accordance with the map, to avoid the contact. Thus, the onboard navigation system 708 is capable of generating and changing the paths of travel the mobile robot's current location and the floor plan location (representing the actual job location in the physical environment) as many times as necessary, to accomplish driving the mobile robot 700 to the actual job location. On the other hand, if the onboard navigation system 708 determines, via its internal path planning engine, that no path to the actual job location exists, it may optionally be programmed to send an error message back to the robot base controller 704, which reports the error condition out to a remote job management system, if appropriate.

The API 716 is operable with the robot base controller 704 and the wireless communication interface 702 to provide information and commands to the robot base controller 704, as well as retrieve job assignment status and route information from the robot base controller 704. For example, if the robot payload 724 needs to send information concerning the status of the cargo in the cargo hold 740 to the job management system (not shown), the cargo information may be transmitted from the robot cargo payload controller 736 to the robot base controller 704 via the API 716. The robot base controller 704 will then transmit the cargo information to the remote job management system through the same API 716. In preferred embodiments, API 716 is ARCL or Arinterface, an application programming interface distributed by Omron Adept Technologies, Inc., of San Ramon, Calif. However, other API's may be suitably adapted and used to provide communication between the mobile robot 700 and other computer systems.

Sensors 706 may comprise a collection of different sensors, such as laser scanners, sonar sensors, bumpers, cameras, gas sensors, smoke sensors, motion sensors, etc., and can be used to perform a variety of different functions. These sensors may also be used for traffic mitigation by redirecting the mobile robot 700 when other mobile robots are detected in the immediate surroundings. Other elements on the robot base include Power 720, which typically includes a battery and software to manage the battery.

The locomotion system 718 includes the hardware and electronics necessary for making the mobile robot 700 move, including, for example, motors, wheels, feedback mechanisms for the motors and wheels, and encoders. The onboard navigation system 708 typically "drives" the mobile robot 700 by sending commands down to the wheels and motors through the locomotion system 718.

The human-machine interface, or HMI 714, typically includes the hardware and electronics, such as buttons, switches, touchscreens, touchpads, speakers, as well as software controllers for buttons, switches, touchscreens, touchpads and speakers, which enable the mobile robot 700 to provide data to and receive commands and other input from humans.

Turning now to the components of the robot payload 724, the cargo sensors 738 provide signals to the robot payload controller 736 and, possibly, directly to robot base controller 704 by means of API 716, which permit the robot payload controller 736 and/or robot base controller 704 to make programmatic decisions about whether the mobile robot 700 has completed an assignment or is available to acquire more cargo. HMI 726 may include buttons, switches, keyboards, touchscreens, etc., or some combination of buttons, switches, keyboards and touchscreens, used to communicate with a human operator. Humans can, for example, use the HMI 726 to input new job requests that would cause the mobile robot 700 proceed to a specified location in the physical environment by selecting the location on the mobile robot's internal map 710. To facilitate selection of a new location, mobile robot 700 may be configured to display locations, floor plans, zones and sectors defined by the map 710 on an HMI 726 comprising a display screen.

Payload sensors 732 may include, for example, temperature or gas sensors, cameras, RFID readers, environmental sensors, wireless Ethernet sniffing sensors, etc. Payload sensors 732 may be used to provide information about the state of the robot payload 724, the state of the cargo in the cargo hold 740, the state of the physical environment, the proximity of the mobile robot 700 to physical objects, or some combination of all of this information.

Actuators 730 may include a wide range of devices, including without limitation, linear actuators, panning and tilting units, articulated mechanical arms, conveyor belts, non-mobile industrial robots, manipulators, lifts, drills, pumps and sprayers, or any other system or device useful for moving, handling, fixing, examining, distributing, collecting, detecting or sampling substances, objects or materials in the physical environment.

The robot payload 724 may also include a wireless communications interface 734, which sends information to and receives information from other devices or networks. Telepresence applications, which permit, for example, physicians to see and speak with patients by using remotely-controlled mobile robots carrying video and audio recording equipment, may use the wireless communications interface 734, for instance, to relay the video and audio signals from the mobile robot 700 to the remotely-located physician.

The robot payload controller 736 processes command and operation signals coming into the robot payload 724 and generally controls and coordinates all of the functions performed by the robot payload 724. In preferred embodiments, the robot payload controller 736 can also cancel a job assignment. For example, if the mobile robot 700 arrives at a specified job location to pick up an item, such as a SMIF pod, and learns through sensors or vision technology attached to the robot payload 724 that the SMIF pod is not present at that location, then the robot payload controller 736 can cancel the job assignment by generating a job cancellation signal and transmitting it to the robot base controller 704 in the robot base 722, along with a string of data that indicates the reason for the cancellation. The robot base controller 704 typically relays that cancellation signal to the job management system to inform the job management system that mobile robot 700 is now available to receive a new job assignment. When it is done with an assignment, the robot payload controller 736 sends a completion signal to the robot base controller 704, or alternatively, toggles a I/O bit in the memory of the robot base 722, which informs the robot base controller 704 that the job assignment is completed.

Figure 8:
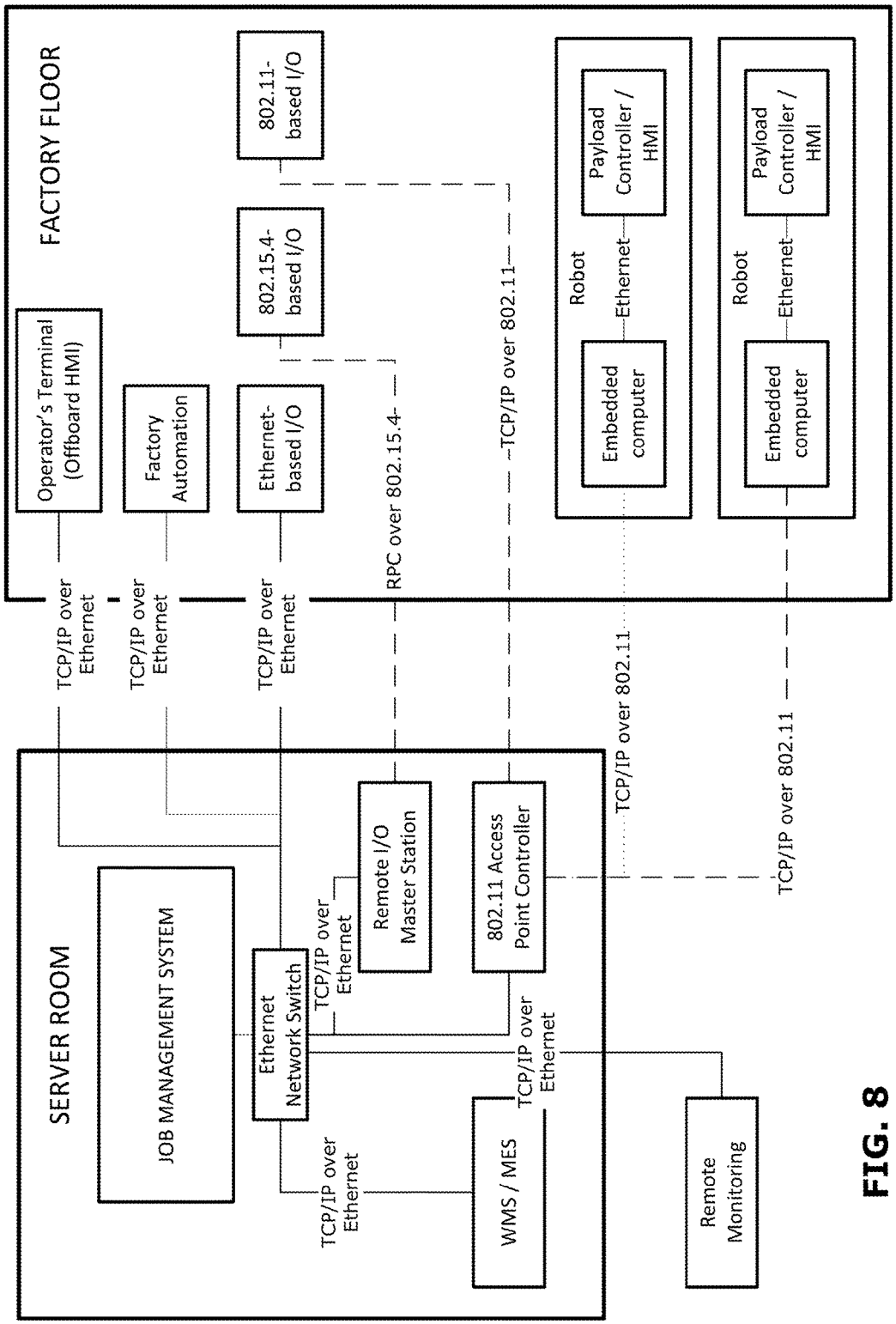
FIGS. 8-12 show high-level block diagrams illustrating the arrangement and connectivity of the major physical components of the automated physical environment shown in FIG. 1.

FIG. 8 shows a high-level block diagram illustrating in more detail the arrangement and connectivity of the major physical components of an automated physical environment, such as the automated physical environment shown in FIG. 1, including physical links and connections between those components. As shown in FIG. 8, a variety of different types of physical connections, including for example, TCP/IP over Ethernet, TCP/IP over 802.11 and RCP over 802.15.4, may be used for communication between devices and computer systems in the physical environment.

Figure 9:
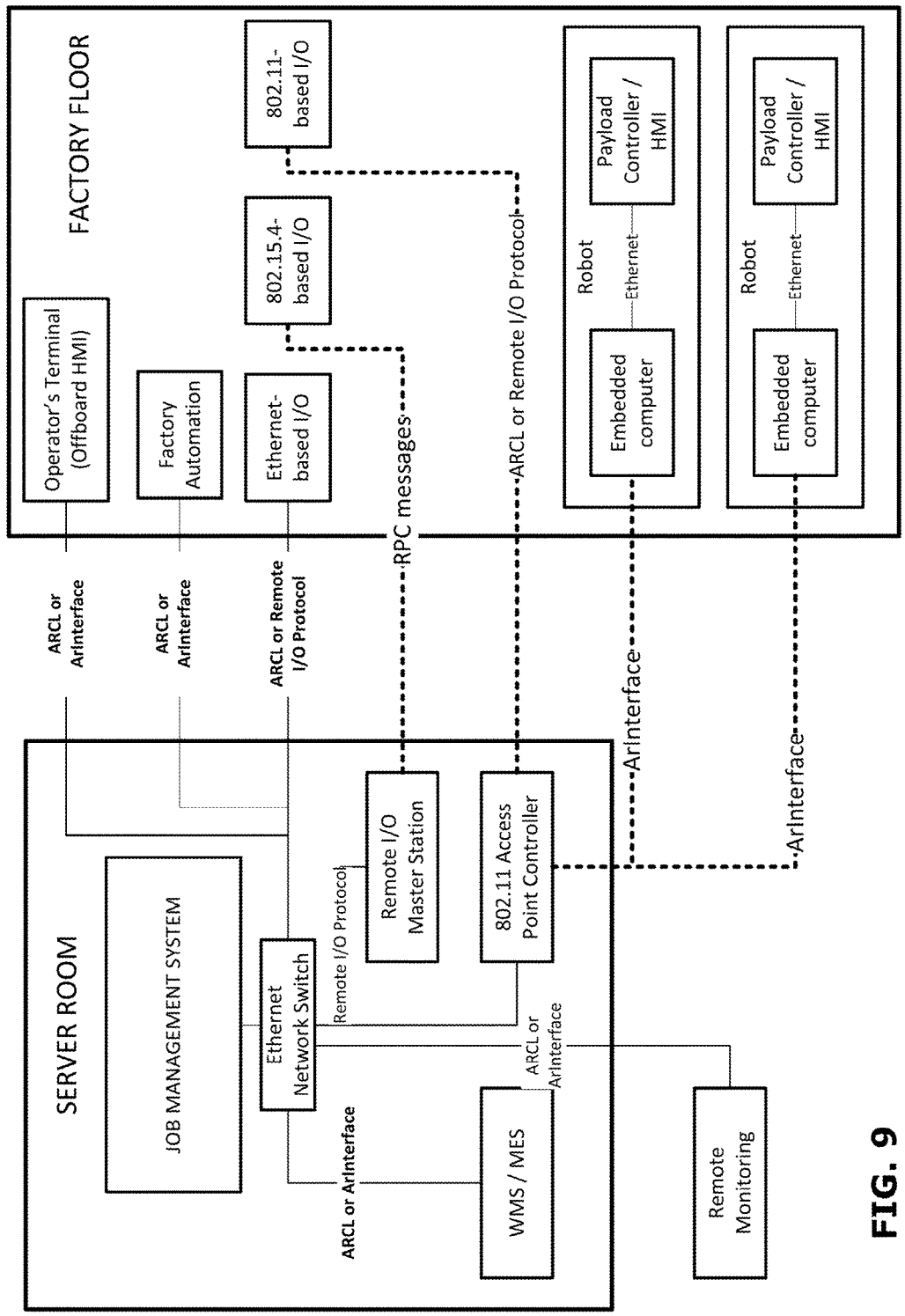

FIG. 9 shows another high-level block diagram illustrating the arrangement and connectivity of the major physical components of the automated physical environment shown in FIG. 1. However, instead of showing the physical connection types, FIG. 9 shows the specific protocols that might be used to communicate over each communication medium.

Figure 10:
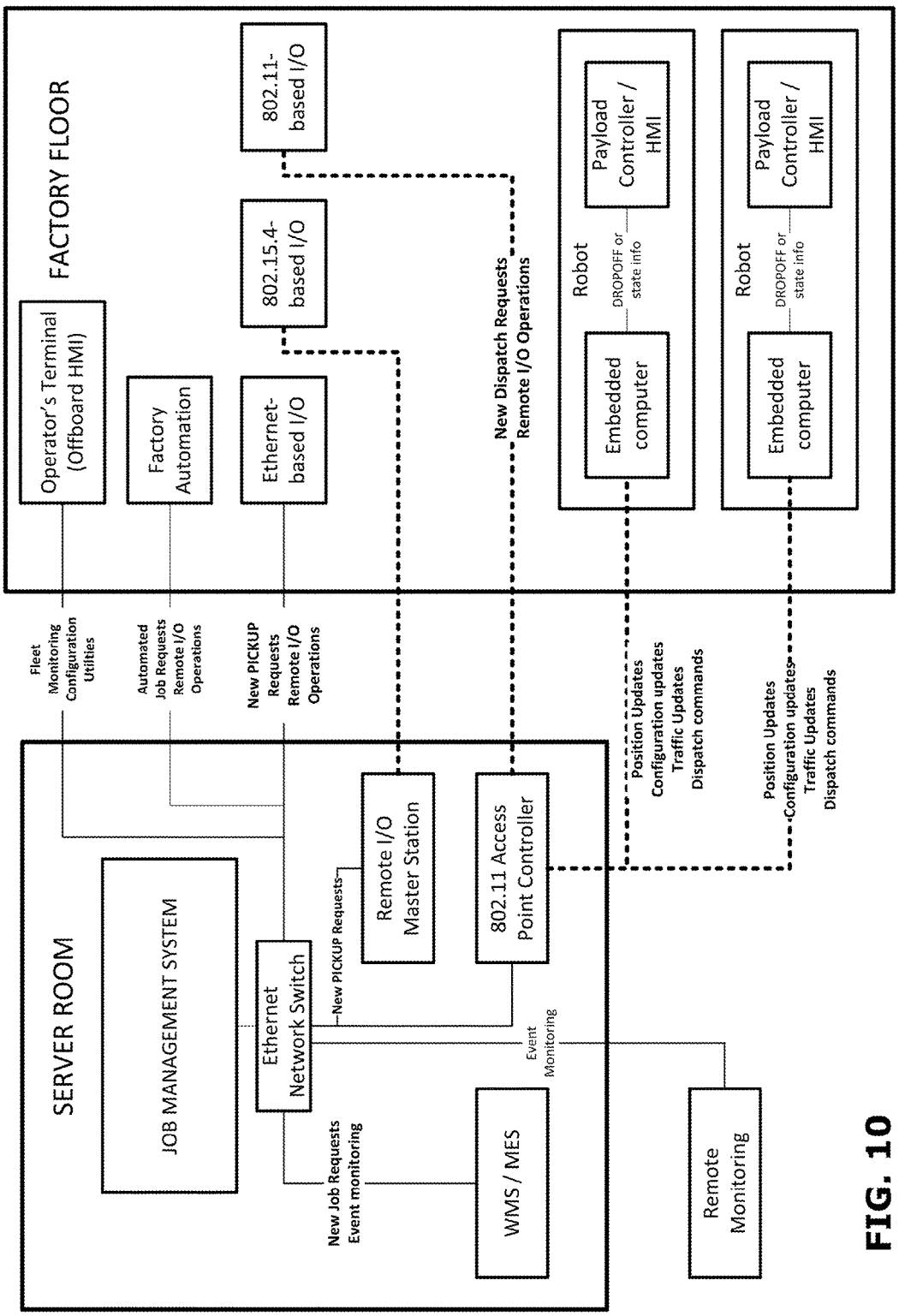

FIG. 10 shows yet another high-level block diagram illustrating the arrangement and connectivity of the major physical components of the automated physical environment shown in FIG. 1. But instead of showing the type of physical connections as in FIG. 8, or the protocol used to communicate over that physical connection as in FIG. 9, FIG. 10 provides a general description of the purpose of each physical connection.

Figure 11:
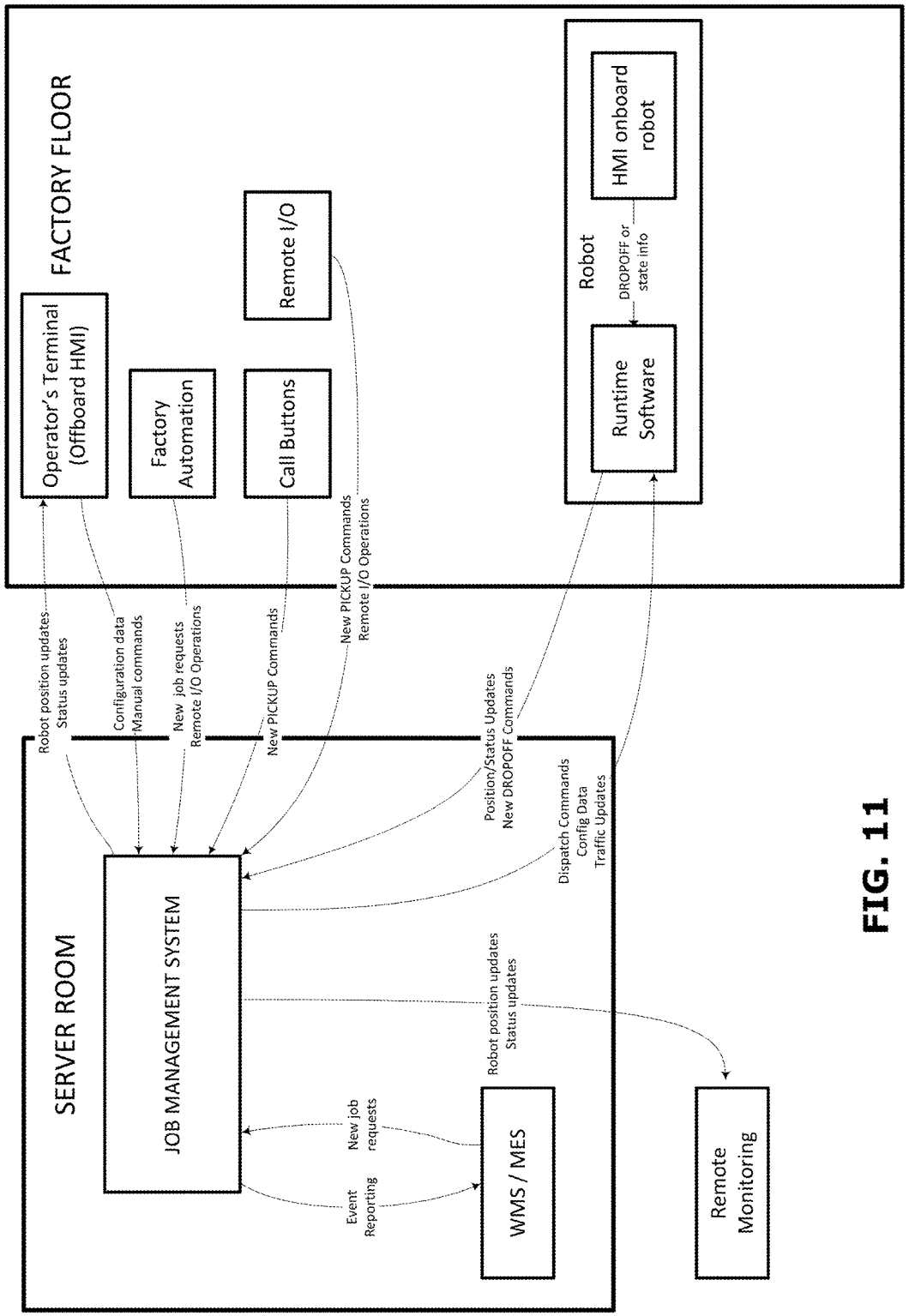

FIG. 11 shows still another high-level block diagram illustrating the arrangement and connectivity of the major physical components of the automated physical environment shown in FIG. 1. But instead of showing the type of physical connections as in FIG. 8, the protocol used to communicate over that physical connection as in FIG. 9, or the general description of the purposes of the physical connections as in FIG. 10, FIG. 11 shows how job requests, commands, status updates, event updates, traffic updates flow between the physical components of the automated physical environment over the physical connections.

Figure 12:
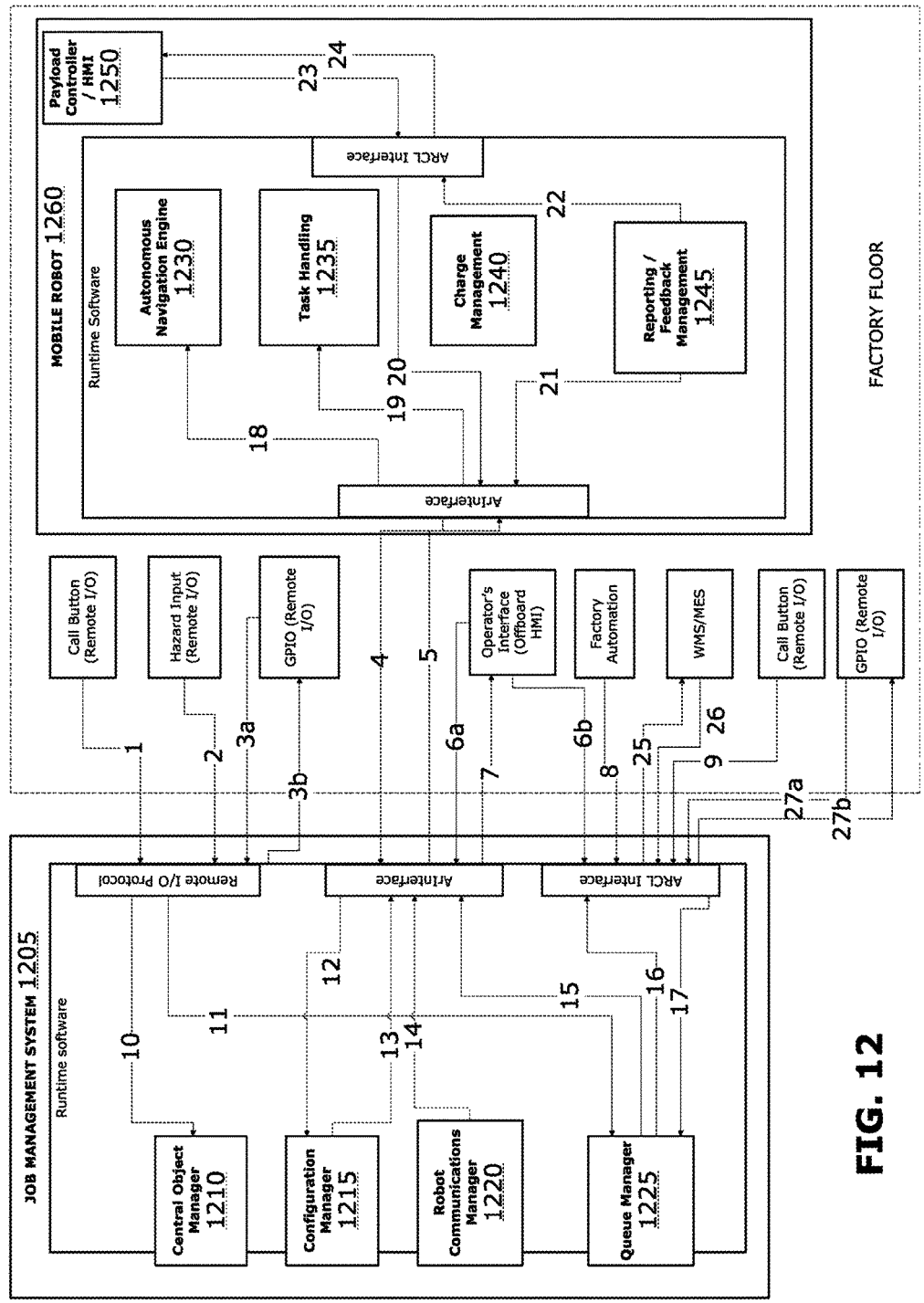

FIG. 12 contains a high-level block diagram illustrating the major functional components of the software modules in exemplary embodiments of an job management system, as well as the major functional components of the software modules executing on an exemplary autonomously-navigating mobile robot, both operating according to the principals of the present invention, as well as the connections between the major functional components in the job management system and the mobile robot. As shown in FIG. 12, the job management system 1205 includes a central object manager 1210, a configuration manager 1215 a robot communications manager 1220 and a queue manager 1225. Central object manager 1210 tracks input/ouput signals, as well as dynamic map objects, such as mobile robot docks, forbidden sectors, etc., and provides this information to each mobile robot in the fleet. Configuration manager 1215 manages the latest map file and operating parameters, and synchronizes them with the maps stored in the memories of the mobile robots. Robot communications manager 1220 tracks mobile robot locations and paths and provides this information to the mobile robots in the fleet, the queue manager 1225 and monitoring stations. Queue manager 1225 receives, prioritizes and dispatches job requests, and provides status updates for job requests.

Mobile robot 1260 includes an autonomous navigation engine 1230, a task handling module 1235, a charge management module 1240, a reporting and feedback management module 1245 and a payload controller/HMI module 1250. The autonomous navigation engine 1230 handles localization, path-planning, obstacle avoidance and similar tasks for the mobile robot 1260. The task handling module 1235 handles execution and mode changes relating to performing non-navigational robotic tasks. Charge management module 1240 monitors and automatically docks the mobile robot when the battery power level is low, and the reporting and feedback management module 1245 provides real-time information about the mobile robot 1260 to the job management system 1205, such as position, velocity, job status and batter level.

The purpose of each one of the physical connections, identified by the labels 1-27 in FIG. 12, is set forth below.
1) Call button presses, which can arrive via a Remote I/O protocol. Button presses are submitted to the Queue Manager 1225 via (11) to be entered into the Queue.
2) Hazard inputs. These can be inputted by an operator or other equipment and are used to signal a predefined condition, such as "aisle 1 is blocked", "STOP all equipment", etc. These inputs are submitted into the Central Object Manager 1210 via (10).
3) General Purpose I/O (GPIO). Link 3a is for submitting inputs from equipment, such as a photo-eye, limit switch, or similar. Link 3b is for setting outputs, such as activating an automatic door-opener, elevator, or conveyor.

4) ArInterface connection from mobile robot 1260 to the job management system 1205. This application programming interface (API) connection that serves as the primary conduit for passing data from the mobile robot 1260 to the job management system 1205. The data may include, for example, inputs from the onboard HMI, real-time status (position, velocity, battery charge, etc), status and event feedback.

5) ArInterface connection from the job management system 1205 to the mobile robot 1260. This API connection is the primary conduit for sending data from the job management system 1205 to the mobile robot 1260. This data may include, for example, map and configuration changes, traffic information about other mobile robots, dispatch commands, changes to global objects, etc.

6a) Input from operator's interface. This can be for the purposes of making changes to the configuration, providing manual controls as would be necessary during maintenance, and commands to interact with the queue (query, cancel, etc).

6b) Input from operator's interface—new queue requests, sent via ARCL to the queue manager 1225.

7) Output from the job management system 1205 to an operator's interface—can provide data such as: robot positions and status, job status, map data, etc.

8) Inputs from Factory Automation—this can be items such as automatically triggered PICKUP or PICKUP-DROPOFF requests from a PLC that is monitoring a tool. Optional feedback can be provided to that equipment, if needed.

9) Inputs from Call Button—Ethernet-based devices can send ARCL commands directly to the job management system 1205. These commands may be used to send direct calls for a mobile robot, and for sending a PICKUP request.

10) Conduit for passing commands received by the Remote I/O incoming interface to a Global Object Manager routine.

11) Conduit for passing commands received by the Remote I/O incoming interface to the queue manager 1225.

12) Conduit for passing commands received to ArInterface to the Configuration Manager 1215. This conduit enables making configuration changes to the system.

13) Conduit for passing configuration data to the connected robots and operator's.

14) Conduit for passing traffic data from the job management system 1205 out to the mobile robot 1260 via an ArInterface API connection.

15) Conduit for passing dispatch commands from the queue manager 1225 out to the mobile robot 1260 via an ArInterface API connection 16) Conduit for passing event updates from the queue manager 1225 out to connected clients (WMS/MES, custom applications, Ethernet-based remote I/O, etc)

17) Conduit for passing incoming queue commands from connected clients (WMS/MES, custom applications, Ethernet-based remote I/O, etc)

18) Conduit for passing information about traffic and global-objects from the job management system 1205 to the Autonomous Navigation Engine 1230.

19) Conduit for passing information from the queue manager 1225 to the mobile robot's 1260 onboard Task Handling module 1235.

20) Conduit for passing locally-generated queue-requests to the ArInterface connection to the job management system 1205. Local queue requests are generated by onboard HMIs, and ultimately end up in the queue onboard the job management system 1205.

21) Conduit for passing status information about the robot back to the job management system 1205. This will be used for functions such as traffic management for determining the most appropriate robot for dispatching.

22) Provides output about the mobile robot 1260 to locally-connected devices. Data could include the mobile robot's current position, velocity, current operating mode, current queue status, etc.

23) Provides input from onboard payload controller and/or HMI devices for generating robot-specific queue requests and providing state information updates (i.e. errors, IO). These requests aren't acted on locally, but rather are passed to the job management system 1205 and put into the main queue.

24) Provides output to the onboard HMI, such as mobile robot status, queue events, etc.

25) Connection from job management system 1205 to the WMS/MES systems. Provides feedback about the status of the queue, and provide event updates as jobs are processed.

26) Connection from WMS/MES to the job management system 1205. This provides incoming dispatch and query requests from the site's primary automation and scheduling management system.

27) Links 27a/b are comparable to links 3a/b, except that they use Ethernet to communicate directly to ARCL on the job management system 1205 instead of the Remote I/O protocol.

Figure 13:
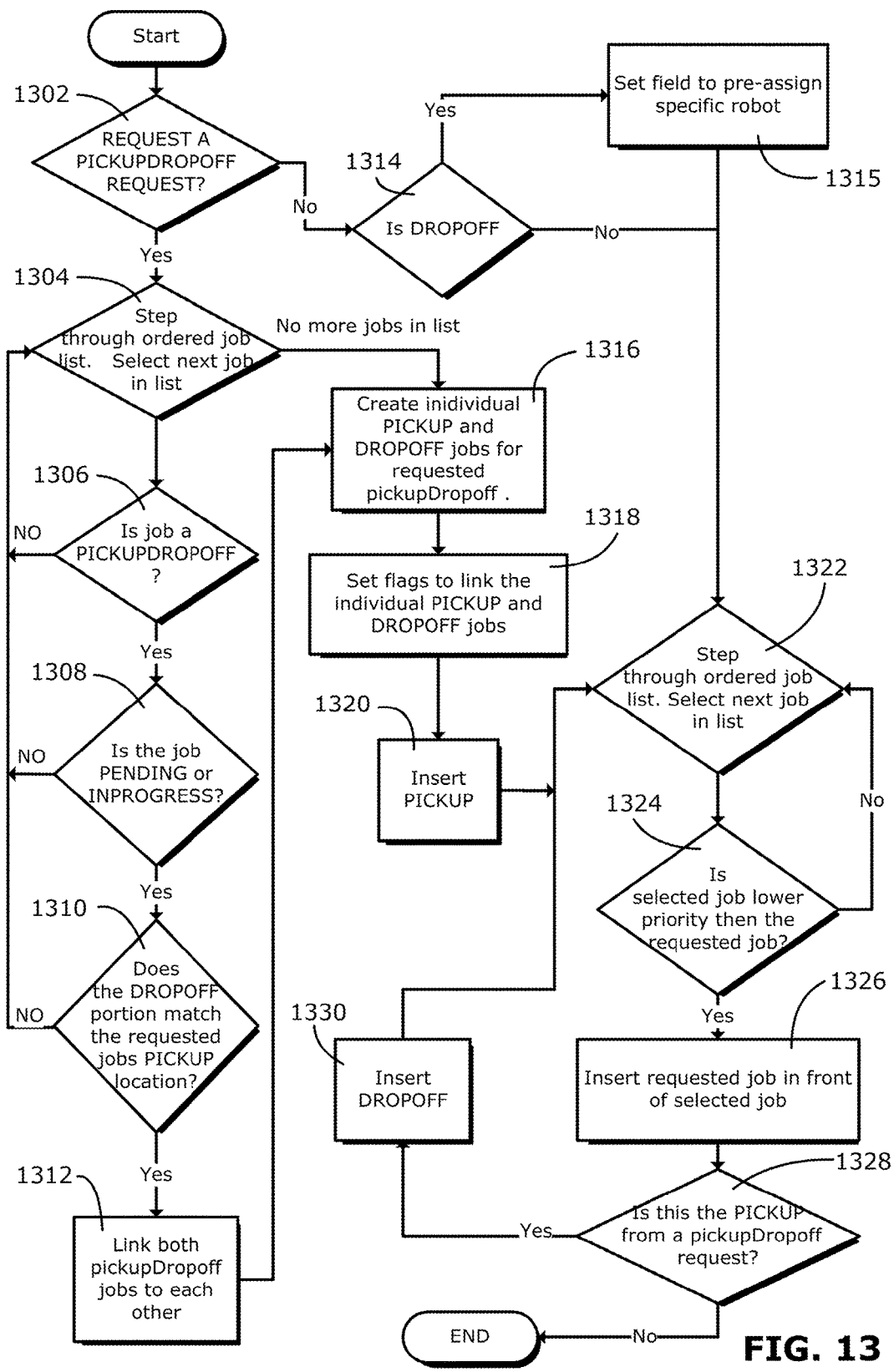
FIGS. 13 and 14 show flow diagrams illustrating exemplary computer-implemented algorithms for prioritizing new job requests and dispatching queued job requests, respectively, by a job management system operating in accordance with embodiments of the present invention.
Figure 14:
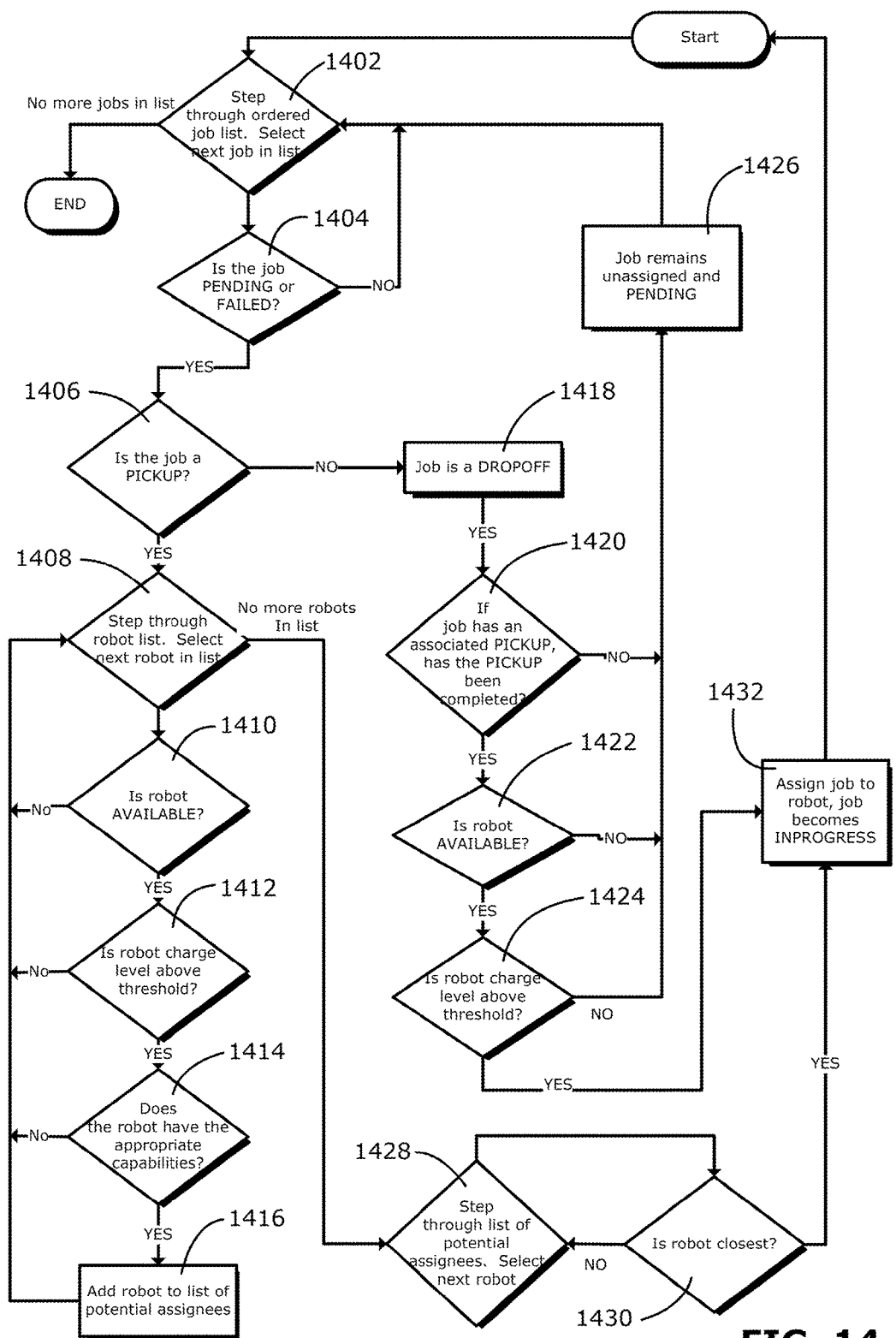
Figure 15:
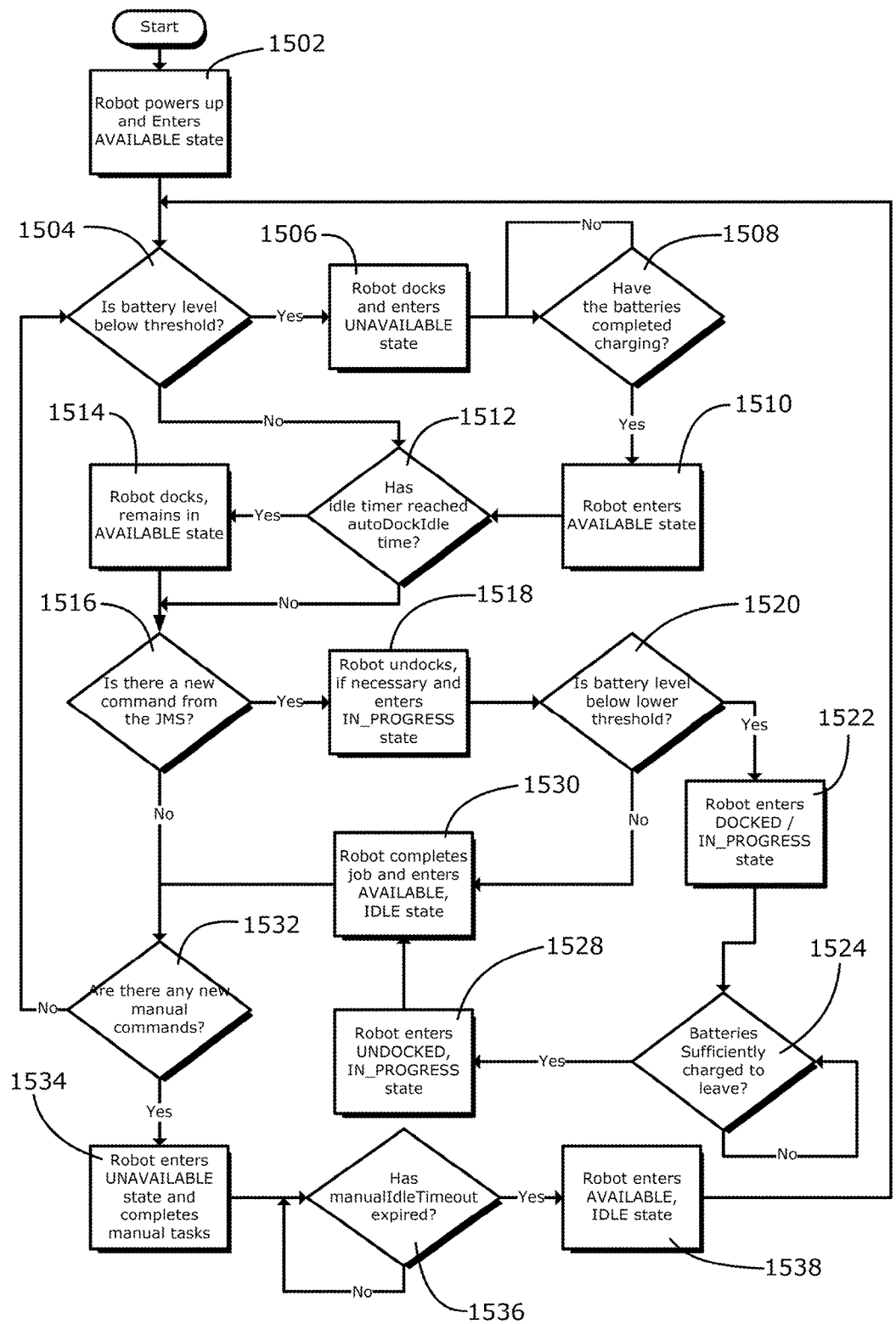
FIG. 15 shows a flow diagram illustrating an exemplary computer-implemented algorithm mobile robots in the fleet of mobile robots might use for charging their batteries and handling job assignments delegated by the job management system in response to received job requests.

FIGS. 13 and 14 show flow diagrams illustrating exemplary computer-implemented algorithms for prioritizing new job requests and dispatching queued job requests, respectively, by a job management system operating in accordance with embodiments of the present invention. FIG. 15 shows a flow diagram illustrating an exemplary computer-implemented algorithm mobile robots in the fleet of mobile robots might use for charging their batteries and handling job assignments delegated by the job management system in response to received job requests. For purposes of the exemplary algorithms, job requests have an associated priority, which may be assigned by a requestor application or otherwise assigned by default. Job requests are also classified as either a "pick up" or as a "drop-off." A pick-up is a job request that can be serviced by any robot; a drop-off is a job request that must be serviced by a specific robot, the assumption being that, when a pick-up is in progress, the selected mobile robot's cargo hold is presumably empty and any mobile robot can handle that pick-up job. Once a mobile robot's payload is loaded with cargo, however, that specific cargo has to go to a particular destination. Therefore, a drop off is always tied to a physical payload on a particular mobile robot.

In preferred embodiments, a single queue manages all the job requests, and a pick-up/drop-off procedure uses the priorities in the queue to carry out a job request. This ensures that all drop-off job request for a specific mobile robot will be performed before any pick-ups. Under the preferred mode of operation, a drop-off job request is not actually queued in the system until after the corresponding pick-up job request has been performed. However, this is not a required mode of operation. Thus, if there is an existing drop-off job in the queue for a particular mobile robot, the drop-off must occur before that mobile robot will be commanded to perform any pick-ups. This ensures that the mobile robot will be unloaded before picking up and loading more cargo.

FIG. 13 shows a high-level flow diagram illustrating the steps that might be performed by the job management system, according to one embodiment of the invention, in order to enter a job request into the queue. As shown in FIG. 13, the system first determines, in steps 1302 and 1314, whether the incoming job request is a pickup/dropoff request, or a pickup or dropoff request. If the incoming request is a pickup/dropoff request, then the system steps through an ordered job list, selecting the next job in the list (step 1304). Next, at step 1306, the system determines if the selected job from the list is a pickup/dropoff. If it is not, then control loops back to step 1304 to select the next job in the list. However, if the job is a pickup/dropoff, then the system determines, in step 1308, whether the selected job is pending or in progress. If the selected job is not pending or in progress, then control again passes back to step 1304 to select another job from the list. However, if it is determined at step 1308 that the job is pending or in progress, then the system determines, in step 1310, whether the dropoff portion of the job matches the requested job's pickup location. If they do not match, then control passes back to step 1304 to select another job from the list. But if there is a match, the system links both pickup/dropoff jobs together (step 1312).

Next, in steps 1316, 1318 and 1320, the system creates individual pickup and dropoff jobs for the requested pickup/dropoff, sets flags to link the individual pickup and dropoff jobs and inserts the pickup portion of the job into the queue. Then, in step 1322, the system again begins to step through the ordered job list by selecting the next job in the list. If the selected job has a priority lower than the priority of the incoming job request, then the incoming job request is inserted into the queue ahead of the selected job, steps 1324 and 1326. Then, if the system determines, in step 1328, that current request is not the pickup portion of a pickup/dropoff request, the processing for the incoming job request ends. But if it is the pickup portion of a pickup/dropoff request, then the system returns to step 1322 to insert the dropoff job into the queue and select the next job in the list. Returning to step 1302, if the incoming request is determined not to be a pickup/dropoff request, the system then determines, in step 1314, if the request is just a dropoff. If so, then the system sets a field in memory indicating that a specific robot should be assigned to handle the job request. If not, then the system next goes to step 1322 to check the priority of the incoming request against the priority of other job requests already in the queue.

FIG. 14 contains a high-level flow diagram that shows an algorithm and illustrates the steps that might be performed by the processor in an job management system, according to one embodiment of the invention, in order to assign job requests to a particular mobile robot in the fleet, taking into account factors such as remaining battery power, robot capabilities (i.e., configuration) and the distance between the mobile robot's current position and the pickup location. Those of ordinary skill in the art will recognize and appreciate that other status and configuration factors could also be used to determine assignments, such as available payload space, traffic conditions along the route, high-priority critical tasks, the required time of arrival, whether deliveries can be batched together, etc. Using a combination of these factors, the system may determine, for example, that the best mobile robot to assign to a particular task may not be the mobile robot that is currently closest in proximity to where that task will be performed.

As shown in FIG. 14, the system maintains an ordered list of job requests (the job request queue) and, in the first step, step 1402, the system selects the next job request in the queue. If there are no more job requests in the queue, then the job request assignment routine stops. But if there is a job request in the queue, the system next determines, based on status information received from mobile robots in the fleet, for example, whether the job is pending or failed (step 1404). If the job is not pending or failed, then control passes back to step 1402, where the next job in the queue is selected for processing. But if the job is pending or failed, then, in step 1406, the system determines if the job is a pickup. If it is a pickup job request, however, the system next goes through status and configuration profile data for all of the mobile robots in the fleet to determine which mobile robots are suitable for the job request based on availability, charge level and capabilities, thereby building a list of potential mobile robot assignees for handling the job request. Steps 1408, 1410, 1414 and 1416. When the list of potential assignees is completed, the system reviews the list to find the mobile robot closest to the job location and assigns that robot to the job request. See steps 1428, 1430 and 1432.

Returning to step 1406, if it is determined that the job in the job request is not a pickup, then it is classified in step 1418 as a dropoff, whereupon the system will next determine whether the dropoff job is associated with a pickup job and whether that pickup job has been completed (step 1420). If an associated and completed pickup portion exists, then the system will assign the job request to the next available mobile robot that is with sufficient battery power (steps 1422, 1424 and 1432). However, if the dropoff job request is not associated with a pickup job request, or if no robot is available, or if no robot has a sufficient battery charge, then the job management system will leave the job unassigned and pending while it returns to the initial step, step 1402, to process more job requests from the queue.

A variety of different approaches can be used to determine the order in which requests are removed from the queue and dispatched to robots for handling. In some embodiments, requests are dispatched according to first in first out (FIFO). In other embodiments, the requests may be dispatched according to a priority flag associated with each request. In still other embodiments the approach combines priority with FIFO (i.e., higher priority jobs are assigned first, and when two jobs have the same priority, the one that arrived first is assigned first). While the algorithm shown in FIG. 14 reflects an approach that combines priority and FIFO, those skilled in the art, upon reading this disclosure, should understand that a different prioritization scheme could be used without departing from the scope of the invention. For example, the job management system may be configured to assign and dispatch requests, taking into account for example, how quickly a nearby robot can arrive at the pickup location, path driving time, and overall performance and throughput of the system.

In preferred embodiments of the job management system, the autonomously-navigating mobile robots are capable of determining when it is time to recharge their batteries, and travel to a charging station to recharge without receiving a specific instruction from the job management system to do so. FIG. 15 shows a high-level flow diagram illustrating an exemplary algorithm that might be executed onboard one or more of the autonomously-navigating mobile robots in the fleet to manage the battery-charging procedure. As shown in FIG. 15, when the mobile robot is powered on, the onboard system identifies the mobile robot as "AVAILABLE." (step 1502). Next, in step 1504, 1506 and 1508, the mobile robot determines whether the battery charge level is below a specified threshold and, if so, changes its status to "UNAVAILABLE" and docks with a battery charging station until recharging is completed, at which point the mobile robot changes its status back to "AVAILABLE" in step 1510. If it is determined in step 1504, however, that the mobile robot's battery already carries a sufficient charge, then the onboard system checks its idle time (step 1512), whether there is a new command from the job management system (step 1516) and whether there are any new manual commands (step 1532) to process.

If there are no new job management system commands or manual commands, processing returns to step 1504, where the battery threshold is rechecked. If, however, there is a new command from the job management system, then the mobile robot enters the "IN PROGRESS" state (step 1518), rechecks the battery level to see if it is below a lower battery threshold (step 1520), and if not, completes the job and re-enters the "AVAILABLE" state (step 1530). But if it is determined at step 1520, that the lower battery threshold has been breached, the mobile robot will dock and charge its battery while remaining in the "IN PROGRESS" state. Step 1522. When the battery charge level is sufficient, step 1524, the mobile robot will automatically undock itself from the recharging station and attempt to complete the job. (Steps 1528 and 1530).

As previously-stated, the job management system of the present invention is typically configured to receive and respond to requests received from a factory scheduling system or other order processing application that is coupled to the JMS via a factory automation system, including without limitation, a local area network (LAN), wide area network (WAN), a corporate intranet or the Internet. Although other methods of exchange commands, responses and data may be used, the JMS and the factory scheduling system (or order processing system) preferably communicate with each other through a collection programmatic function calls (also known as an "application programming interface," or API). An exemplary collection of function calls suitable for this purpose is provided below.

```
QueueCancel
   Description:
      Cancels an item that is in the queue
   Usage:
      queuecancel <canceltype> <cancelvalue> [echo_string] [reason]
   Arguments:
      <canceltype> can be <id> <jobid> <robotname> <status>
      Valid <cancelvalues> for <canceltype>=status are <inprogress> <pending>
      <interrupted>
      If [echo_string] is provided, then it will be returned back with any responses
      generated from this command. Can be used as a "Transaction ID"
      [reason] is an optional string that can be used to provide a reason for cancellation
   Returns (for a pending item):
      queuecancel cancelling <cancelvalue> <canceltype> <echostring> <reason> from
      queue
      QueueCancel: <id> <jobid> <priority> <status = Cancelled> <subStatus = None>
   Goal
      <"goal_name"> <"robotname"> <queued date> <queued time> <completed date>
      <completed time> <echostring>
   Returns (for an in progress item):
      queuecancel cancelling <cancelvalue> <canceltype> <echostring> <reason> from
      queue
      QueueCancel: <id> <jobid> <priority> <status = Cancelling> <subStatus = =
      reason_or_None > Goal <"goal_name"> <"robotname"> <queued date> <queued
      time> <completed date = None> <completed time = None> <echostring>
      QueueUpdate: <id> <jobid> <priority> <status = Interrupted> <subStatus = =
      reason_or_None > Goal <"goal_name"> <"robotname"> <queued date> <queued
      time> <completed date = None> <completed time = None> <failed count>
      QueueUpdate: <id> <jobid> <priority> <status = Cancelled> <subStatus = =
      reason_or_None > Goal <"goal_name"> <"robotname"> <queued date> <queued
      time> <completed date> <completed time> <failed count>
QueuePickup
   Description:
      Instructs the Job Management System that a new PICKUP is requested at a particu-
lar
      goal. Any robot will respond.
   Usage:
      queuepickup <goal_name> [priority] [job_id]
   Arguments:
      If [priority] is not assigned then a default one will be used.
      If [job_id] is not assigned then a default one will be used
   Returns:
      queuepickup goal <"goal_name"> with priority <priority>, id <id> and
      job_id <job_id> successfully queued
      QueueUpdate: <id> <job_id> <priority> <status = Pending> <substatus = None>
   Goal
      <"goal_name"> <assigned robot_name = None> <queued date> <queued time>
      <completed date = None> <completed time = None> <failed count>
      QueueUpdate: <id> <job_id> <priority> <status = InProgress> <substatus = None>
      Goal <"goal_name"> <"robot_name"> <queued date> <queued time> <completed
      date = None> <completed time = None> <failed count>
      QueueUpdate: <id> <job_id> <priority> <status = Completed> <substatus = None>
      Goal <"goal_name"> <"robot_name"> <queued date> <queued time> <completed
      date> <completed time> <failed count>
```

QueuePickupDropoff
  Description:
    Instructs the Job Management System that a new PICKUP is requested at a particular
    goal (PICKUPgoal_name), and that the DROPOFF should be at a predetermined goal
    (DROPOFFgoal_name). Any robot will respond.
  Usage:
    queuepickupdropoff <PICKUPgoal_name> <DROPOFFgoal_name>
    [PICKUPpriority] [DROPOFFpriority] [job_id]
  Arguments:
    If [PICKUPpriority] or [DROPOFFpriority] are not assigned then default ones will be
    used.
    If [job_id] is not assigned then a default one will be used
  Returns:
    queuepickupdropoff goals <"PICKUPgoal"> and <"DROPOFFgoal"> with priorities
    <PICKUPpriority> and <DROPOFFpriority> ids <PICKUPid> and <DROPOFFid>
    job_id <jobid> successfully queued
    QueueUpdate: <id> <job_id> <priority> <status=Pending> <substatus=None> Goal
    <"goal_name"> <robot_name> <queued date> <queued time> <completed
    date=None> <completed time=None> <failed count>
    QueueUpdate: <id> <job_id> <priority> <status=InProgress> <substatus=None>
    Goal
    <"goal_name"> <robot_name> <queued date> <queued time> <completed
    date=None> <completed time=None> <failed count>
    QueueUpdate: <id> <job_id> <priority> <status=Completed> <substatus=None>
    Goal <"goal_name"> <robot_name> <queued date> <queued time> <completed
    date> <completed time> <failed count>
    QueueUpdate: <id> <job_id> <priority> <status=InProgress> <substatus=None>
    Goal
    <"goal_name"> <robot_name> <queued date> <queued time> <completed
    date=None> <completed time=None> <failed count>
    QueueUpdate: <id> <job_id> <priority> <status=Completed> <substatus=None>
    Goal <"goal_name"> <robot_name> <queued date> <queued time> <completed
    date> <completed time> <failed count>
QueueQuery
  Description:
    Queries the status of the entries in the Job Management System's queues. Items
    can be selected with a variety of criteria, such as JobID, goal, robotname, etc
  Usage:
    queuequery <querytype> <queryvalue> [echo_string]
  Arguments:
    <querytype> can be <id> <jobid> <goal> <robotname> <status> <priority>
    <queryvalue> for querytype=status are <inprogress> <pending> <interrupted>
    <completed> <cancelled> <failed> <docked>
    If [echo_string] is provided, then it will be returned back with any responses
    generated from this command. Can be used as a "Transaction ID"
  Returns:
    QueueQuery: <id> <jobid> <priority> <status> <substatus> Goal <"goal_name">
    <robotName> <queued date> <queued time> <completed date> <completed time>
    <echostring> <failed count>
QueueShow
  Description:
    Reports all of the entries in the queue, including the status of each robot in the fleet
  Usage:
    queueshow [echo_string]
  Arguments:
    If [echo_string] is provided, then it will be returned back with any responses
    generated from this command. Can be used as a "Transaction ID"
  Returns:
    QueueRobot: <robotname> <robotstatus> <robotsubstatus> <echo_string>
    QueueRobot: <robotname> <robotstatus> <robotsubstatus> <echo_string>
    QueueShow: <id> <jobid> <priority> <status> <substatus> Goal <"goal_name">
    <"robotName"> <queued date> <queued time> <completed date> <completed
    time> <echostring> <failed count>
QueueShowRobot
  Description:
    Reports the status of all robots in the fleet
  Usage:
    queueshowrobot [robot_name_or_"default"] [echo_string]
  Arguments:
    If [robot_name] is provided then it returns the status of that particular robot. If field
    is blank, or is "default", then it returns the status of all robots in the fleet.
    If [echo_string] is provided, then it will be returned back with any responses
    generated from this command. Can be used as a "Transaction ID"
  Returns:
    QueueRobot: <robotname> <robotstatus> <robotsubstatus> <echostring>

States & Substates

Job States
The following states and substates apply to the job, and also to the robot where relevant:
Pending None
Available Available
Interrupted None
InProgress UnAllocated
InProgress Allocated
InProgress BeforePickup
InProgress BeforeDropoff
InProgress EveryBefore
InProgress Before
InProgress Driving
InProgress After
InProgress EveryAfter
InProgress AfterPickup
InProgress AfterDropoff
Completed None
Additional Robot States
The following additional states apply to robot's that do not have an assigned job:
Available Available
UnAvailable NotUsingEnterpriseManager
UnAvailable UnknownBatteryType
UnAvailable Forced Docked
UnAvailable Lost
UnAvailable EStopPressed
UnAvailable Interrupted
UnAvailable InterruptedButNotYetIdle
UnAvailable Fault_Driving_Application_<application_provided_string>

Data types

| Argument | Data Type | Length |
| --- | --- | --- |
| canceltype | string | 127 |
| cancelvalue | string | 127 |
| echo_string | string | 127 |
| reason | string | 127 |
| querytype | string | 127 |
| queryvalue | string | 127 |
| PICKUPgoal_name | string | 127 |
| DROPOFFgoal_name | string | 127 |
| job_id | string | 127 |
| goal_name | string | 127 |
| PICKUPpriority | integer (signed long) | −2147483648 to 2147483647 |
| DROPOFFpriority | integer (signed long) | −2147483648 to 2147483647 |
| priority | integer (signed long) | −2147483648 to 2147483647 |

Job ID
If the job is not provided then it is automatically generated in the following format:
JOBxx ARCL Commands that are Enabled on Each Robot:

QueueCancelLocal
  Description:
    Same as QueueCancel on Job Management System, but only applies to items
    queued for this particular robot
QueueDropoff
  Description:
    Instructs a robot to make a DROPOFF at a certain goal. Should only be used from
    onboard User-Interface, such as onboard touchscreen or PLC.
  Usage:
    queuedropoff <goal_name> [priority] [job_id]
  Returns:
    queuedropoff attempting to queue goal <goal_name> <priority> <job_id>
    queuedropoff goal <goal_name> with priority <priority>, id <id> and job_id
<job_id>
    successfully queued to Fleet Manager
    QueueUpdate: <id> <job_id> <priority> <status> <substatus> Goal
    <goal_name> <robot_name> <queued date> <queued time> <completed date>
    <completed time> <failed count>
QueueQueryLocal
  Description:
    Queries the status of the entries in the Job Management System's queues. Items
    can be selected with a variety of criteria, such as JobID, goal, robotname, etc

```
Usage:
    queuequerylocal <querytype> <queryvalue> [echo_string]
Arguments:
    <querytype> can be <id> <jobid> <goal> <robotname> <status> <priority>
    <queryvalue> for querytype=status are <inprogress> <pending> <interrupted>
    <completed> <cancelled> <failed> <docked>
    If [echo_string] is provided, then it will be returned back with any responses
    generated from this command. Can be used as a "Transaction ID"
Returns:
    QueueQuery: <id> <jobid> <priority> <status> <substatus> Goal <"goal_name">
    <robotName> <queued date> <queued time> <completed date> <completed time>
    <echostring>
QueueShowRobotLocal
    Description:
        Queries the status the robot.
    Usage:
        queueshowrobotlocal [echo_string]
    Arguments:
        If [echo_string] is provided, then it will be returned back with any responses
        generated from this command. Can be used as a "Transaction ID"
    Returns:
        QueueRobot: <robotname> <robotstatus> <robotsubstatus> <echostring>
```

EXAMPLES

Following are several examples to demonstrate usage of the various commands. Lines that start with "QueueUpdate:" are messages that are broadcasted by the Job Management System.

QueueCancel Examples

```
Example #1—cancelling a Pending item:
    QueueUpdate: PICKUP11 JOB11 10 Pending None Goal "t" None
    12/19/2011 06:50:45 None None 0
    queuecancel goal t abc
    QueueCancel: PICKUP11 JOB11 10 Cancelling None Goal "w20" None
    12/16/2011 13:19:07 None None abc
    QueueUpdate: PICKUP11 JOB11 10 Cancelled None Goal "t" None
    12/19/2011 06:50:45 12/19/2011 06:50:58 0
Example #2—cancelling an InProgress item
    QueueUpdate: PICKUP8 JOB8 10 InProgress None Goal "w20"
    "MT-490" 12/16/2011 13:19:07 None None 0
    queuecancel goal w20 abc
    QueueCancel: PICKUP8 JOB8 10 Cancelling None Goal "w20" None
    12/16/2011 13:19:07 None None abc
    QueueUpdate: PICKUP8 JOB8 10 Interrupted None Goal "w20" None
    12/16/2011 13:19:07 None None 0
    QueueUpdate: PICKUP8 JOB8 10 Cancelled None Goal "w20" None
    12/16/2011 13:19:07 12/16/2011 13:19:13 0
Example #3—cancelling an InProgress item with reason
    QueueUpdate: PICKUP8 JOB8 10 InProgress None Goal "w20"
    "MT-490" 12/16/2011 13:19:07 None None 0
    queuecancel goal w20 abc cancelreason
    QueueCancel: PICKUP8 JOB8 10 Cancelling cancelreason Goal "w20"
    None 12/16/2011 13:19:07 None None abc
    QueueUpdate: PICKUP8 JOB8 10 Interrupted None Goal "w20" None
    12/16/2011 13:19:07 None None 0
    QueueUpdate: PICKUP8 JOB8 10 Cancelled cancelreason Goal "w20"
    None 12/16/2011 13:19:07 12/16/2011 13:19:13 0
```

QueuePickup Examples

```
Example #1—queuepickup with priority and JobID
    queuepickup z 11 xyz
    queuepickup goal "z" with priority 11, id PICKUP13 and job_id xyz
    successfully queued
    QueueUpdate: PICKUP13 xyz 11 Pending None Goal "z" None
    12/19/2011 06:54:18 None None 0
    QueueUpdate: PICKUP13 xyz 11 InProgress UnAllocated Goal "z" None
    12/19/2011 06:54:18 None None 0
    QueueUpdate: PICKUP13 xyz 11 InProgress Allocated Goal "z" None
    12/19/2011 06:54:18 None None 0
    QueueUpdate: PICKUP13 xyz 11 InProgress BeforePickup Goal "z"
    "Adept_Telepresence_Robot" 12/19/2011 06:54:18 None None 0
    QueueUpdate: PICKUP13 xyz 11 InProgress EveryBefore Goal "z"
    "Adept_Telepresence_Robot" 12/19/2011 06:54:18 None None 0
    QueueUpdate: PICKUP13 xyz 11 InProgress Before Goal "z"
    "Adept_Telepresence_Robot" 12/19/2011 06:54:18 None None 0
    QueueUpdate: PICKUP13 xyz 11 InProgress Driving Goal "z"
    "Adept_Telepresence_Robot" 12/19/2011 06:54:18 None None 0
    QueueUpdate: PICKUP13 xyz 11 InProgress After Goal "z"
    "Adept_Telepresence_Robot" 12/19/2011 06:54:18 None None 0
    QueueUpdate: PICKUP13 xyz 11 InProgress AfterEvery Goal "z"
    "Adept_Telepresence_Robot" 12/19/2011 06:54:18 None None 0
    QueueUpdate: PICKUP13 xyz 11 InProgress AfterPickup Goal "z"
    None 12/19/2011 06:54:18 None None 0
    QueueUpdate: PICKUP13 xyz 11 Completed None Goal "z"
    "Adept_Telepresence_Robot" 12/19/2011 06:54:18 12/19/2011 06:54:34
    0
Example #2—queuepickup with default priority and JobID
    queuepickup x default myjob1
    queuepickup goal "x" with priority 10, id PICKUP14 and job_id
    myjob1
    successfully queued
    QueueUpdate: PICKUP14 myjob1 10 Pending None Goal "x" None
    12/19/2011 06:56:13 None None 0
    QueueUpdate: PICKUP14 myjob1 10 InProgress UnAllocated Goal "x"
    "Adept_Telepresence_Robot" 12/19/2011 06:56:13 None None 0
    QueueUpdate: PICKUP14 myjob1 10 InProgress Allocated Goal "x"
    "Adept_Telepresence_Robot" 12/19/2011 06:56:13 None None 0
    QueueUpdate: PICKUP14 myjob1 10 InProgress Driving Goal "x"
    "Adept_Telepresence_Robot" 12/19/2011 06:56:13 None None 0
    QueueUpdate: PICKUP14 myjob1 10 Completed None Goal "x"
    "Adept_Telepresence_Robot" 12/19/2011 0 6:56:13 12/19/2011 06:56:30
    0
Example #3—queuepickup with default priority and default JobID
    queuepickup t
    queuepickup goal "t" with priority 10, id PICKUP15 and job_id JOB15
    successfully queued
    QueueUpdate: PICKUP15 JOB15 10 Pending None Goal "t" None
    12/19/2011 06:58:12 None None 0
    QueueUpdate: PICKUP15 JOB15 10 InProgress UnAllocated Goal "t"
    "MT-490" 12/19/2011 06:58:12 None None 0
    QueueUpdate: PICKUP15 JOB15 10 InProgress Allocated Goal "t"
    "MT-490" 12/19/2011 06:58:12 None None 0
    QueueUpdate: PICKUP15 JOB15 10 InProgress Driving Goal "t"
    "MT-490" 12/19/2011 06:58:12 None None 0
```

QueueUpdate: PICKUP15 JOB15 10 Completed None Goal "t" "MT-490" 12/19/2011 06:58:12 12/19/2011 06:58:12 0

QueuePickupDropoff Examples

Example #1—queuepickupdropoff with priority1 and priority2 and JobID
queuepickupdropoff x y 10 11 abc
queuepickupdropoff goals "x" and "y" with priorities 10 and 11 ids PICKUP22 and DROPOFF23 job_id abc successfully queued
QueueUpdate: PICKUP22 abc 10 Pending None Goal "x" None 12/19/2011 07:24:02 None None 0
QueueUpdate: DROPOFF23 abc 11 Pending None Goal "y" "None" 12/19/2011 07:24:29 None None 0
QueueUpdate: PICKUP22 abc 10 InProgress UnAllocated Goal "x" "Adept_Telepresence_Robot" 12/19/2011 07:24:02 None None 0
QueueUpdate: PICKUP22 abc 10 InProgress Allocated Goal "x" "Adept_Telepresence_Robot" 12/19/2011 07:24:02 None None 0
QueueUpdate: PICKUP22 abc 10 InProgress Driving Goal "x" "Adept_Telepresence_Robot" 12/19/2011 07:24:02 None None 0
QueueUpdate: PICKUP22 abc 10 Completed None Goal "x" "Adept_Telepresence_Robot" 12/19/2011 07:24:02 12/19/2011 07:24:29 0
QueueUpdate: DROPOFF23 abc 11 InProgress UnAllocated Goal "y" "Adept_Telepresence_Robot" 12/19/2011 07:24:29 None None 0
QueueUpdate: DROPOFF23 abc 11 InProgress Allocated Goal "y" "Adept_Telepresence_Robot" 12/19/2011 07:24:29 None None 0
QueueUpdate: DROPOFF23 abc 11 InProgress Driving Goal "y" "Adept_Telepresence_Robot" 12/19/2011 07:24:29 None None 0
QueueUpdate: DROPOFF23 abc 11 Completed None Goal "y" "Adept_Telepresence_Robot" 12/19/2011 07:24:29 12/19/2011 07:24:52 0
Example #1—Pod swapped
queuepickupdropoff x y
queuepickupdropoff goals "x" and "y" with priorities 10 and 20 ids PICKUP12 and DROPOFF13 job_id JOB12 successfully queued
QueueUpdate: PICKUP12 JOB12 10 Pending None Goal "x" "None" 08/16/2012 14:32:54 None None 0
QueueUpdate: DROPOFF13 JOB12 20 Pending None Goal "y" "None" 08/16/2012 14:32:54 None None 0
QueueUpdate: PICKUP12 JOB12 10 InProgress UnAllocated Goal "x" "mt400" 08/16/2012 14:32:54 None None 0
queuepickupdropoff y t
queuepickupdropoff goals "y" and "t" with priorities 10 and 20 ids PICKUP14 and DROPOFF15 job_id JOB14 successfully queued
QueueUpdate: PICKUP14 JOB14 10 Pending None Goal "y" "mt400" 08/16/2012 14:33:01 None None 0
QueueUpdate: DROPOFF15 JOB14 20 Pending None Goal "t" "mt400" 08/16/2012 14:33:01 None None 0
QueueUpdate: PICKUP12 JOB12 10 InProgress Allocated Goal "x" "mt400" 08/16/2012 14:32:54 None None 0
QueueUpdate: PICKUP12 JOB12 10 InProgress Driving Goal "x" "mt400" 08/16/2012 14:32:54 None None 0
QueueUpdate: PICKUP12 JOB12 10 Completed None Goal "x" "mt400" 08/16/2012 14:32:54 08/16/2012 14:33:15 0
QueueUpdate: DROPOFF13 JOB12 20 InProgress UnAllocated Goal "y" "mt400" 08/16/2012 14:32:54 None None 0
QueueUpdate: DROPOFF13 JOB12 20 InProgress Allocated Goal "y" "mt400" 08/16/2012 14:32:54 None None 0
QueueUpdate: DROPOFF13 JOB12 20 InProgress Driving Goal "y" "mt400" 08/16/2012 14:32:54 None None 0
QueueUpdate: DROPOFF13 JOB12 20 Completed None Goal "y" "mt400" 08/16/2012 14:32:54 08/16/2012 14:33:27 0
QueueUpdate: PICKUP14 JOB14 10 Completed None Goal "y" "mt400" 08/16/2012 14:33:01 08/16/2012 14:33:27 0
QueueUpdate: DROPOFF15 JOB14 20 InProgress UnAllocated Goal "t" "mt400" 08/16/2012 14:33:01 None None 0
QueueUpdate: DROPOFF15 JOB14 20 InProgress Allocated Goal "t" "mt400" 08/16/2012 14:33:01 None None 0
QueueUpdate: DROPOFF15 JOB14 20 InProgress Driving Goal "t" "mt400" 08/16/2012 14:33:01 None None 0
QueueUpdate: DROPOFF15 JOB14 20 Completed None Goal "t" "mt400" 08/16/2012 14:33:01 08/16/2012 14:33:35 0

QueueQuery Examples

Example queuequery status completed xyz
QueueQuery: DROPOFF18 y4rt 22 Completed None Goal "x" "MT-490" 12/19/2011 07:07:53 12/19/2011 07:08:07 xyz 0
QueueQuery: DROPOFF16 abc 20 Completed None Goal "x" "MT-490" 12/19/2011 07:06:00 12/19/2011 07:06:16 xyz 0
QueueQuery: DROPOFF17 JOB17 20 Completed None Goal "z" "MT-490" 12/19/2011 07:06:21 12/19/2011 07:06:35 xyz 0
QueueQuery: DROPOFF19 yyy 20 Completed None Goal "x" "MT-490" 12/19/2011 07:08:49 12/19/2011 07:08:49 xyz 0
QueueQuery: DROPOFF20 yyy 20 Completed None Goal "x" "MT-490" 12/19/2011 07:09:08 12/19/2011 07:09:09 xyz 1
QueueQuery: DROPOFF21 JOB21 20 Completed None Goal "x" "MT-490" 12/19/2011 07:09:33 12/19/2011 07:09:34 xyz 0
QueueQuery: PICKUP12 xyz 11 Completed None Goal "t" "MT-490" 12/19/2011 06:53:51 12/19/2011 06:54:02 xyz 5
QueueQuery: PICKUP13 xyz 11 Completed None Goal "z" "Adept_Telepresence_Robot" 12/19/2011 06:54:18 12/19/2011 06:54:34 xyz 0

QueueShow Examples

Example

QueueRobot: "Adept_Telepresence_Robot" Unavailable InterruptedButNotYetIdle ""
QueueRobot: MT-490 Available Available ""
QueueRobot: MT-490 Available Available ""
QueueRobot: "patrolbot" UnAvailable Fault_Driving_Application_faultName ""
QueueShow: PICKUP22 abc 10 Completed None Goal "x" "Adept_Telepresence_Robot" 12/19/2011 07:24:02 12/19/2011 07:24:29 "" 2

QueueDropoff Examples

Example #1—queuedropoff with priority and JobID
queuedropoff x 22 y4rt
queuedropoff attempting to queue goal "x" with priority 22
queuedropoff goal "x" with priority 22, id DROPOFF18 and job_id y4rt successfully queued to Fleet Manager
QueueUpdate: DROPOFF18 y4rt 22 Pending None Goal "x" "MT-490" 12/19/2011 07:07:53 None None 0
Going to X
QueueUpdate: DROPOFF18 y4rt 22 InProgress UnAllocated Goal "x" "MT-490" 12/19/2011 07:07:53 None None 0
QueueUpdate: DROPOFF18 y4rt 22 InProgress Allocated Goal "x" "MT-490" 12/19/2011 07:07:53 None None 0
QueueUpdate: DROPOFF18 y4rt 22 InProgress BeforeDropoff Goal "x" "MT-490" 12/19/2011 07:07:53 None None 0
QueueUpdate: DROPOFF18 y4rt 22 InProgress EveryBefore Goal "x" "MT-490" 12/19/2011 07:07:53 None None 0
QueueUpdate: DROPOFF18 y4rt 22 InProgress Before Goal "x" "MT-490" 12/19/2011 07:07:53 None None 0
QueueUpdate: DROPOFF18 y4rt 22 InProgress Driving Goal "x" "MT-490" 12/19/2011 07:07:53 None None 0
QueueUpdate: DROPOFF18 y4rt 22 InProgress After Goal "x" "MT-490"

-continued

```
12/19/2011 07:07:53 None None 0
QueueUpdate: DROPOFF18 y4rt 22 InProgress AfterEvery Goal "x"
"MT-490" 12/19/2011 07:07:53 None None 0
QueueUpdate: DROPOFF18 y4rt 22 InProgress AfterPickup Goal "x"
"MT-490" 12/19/2011 07:07:53 None None 0
Arrived at X
QueueUpdate: DROPOFF18 y4rt 22 Completed None Goal "x" "MT-
490"
01/19/2011 07:07:53 01/19/2011 07:08:07 0
Example #2—queuedropoff with default priority and JobID
  queuedropoff x default yyy
  queuedropoff attempting to queue goal "x" using default priority
  queuedropoff goal "x" with priority 20, id DROPOFF20 and job_id yyy
  successfully queued to Fleet Manager
  QueueUpdate: DROPOFF20 yyy 20 Pending None Goal "x" "MT-490"
12/19/2011 07:09:08 None None 0
Going to X
QueueUpdate: DROPOFF20 yyy 20 InProgress UnAllocated Goal "x"
"MT-490" 12/19/2011 07:09:08 None None 0
QueueUpdate: DROPOFF20 yyy 20 InProgress Allocated Goal "x"
"MT-490" 12/19/2011 07:09:08 None None 0
QueueUpdate: DROPOFF20 yyy 20 InProgress Driving Goal "x"
"MT-490" 12/19/2011 07:09:08 None None 0
Arrived at X
QueueUpdate: DROPOFF20 yyy 20 Completed None Goal "x"
"MT-490" 12/19/2011 07:09:08 12/19/2011 07:09:09 0
Example #3—queuedropoff with default priority and default JobID
  queuedropoff x
  queuedropoff attempting to queue goal "x" using default priority
  queuedropoff goal "x" with priority 20, id DROPOFF21 and job_id
  JOB21 successfully queued to Fleet Manager
  QueueUpdate: DROPOFF21 JOB21 20 Pending None Goal "x" "MT-
490"
12/19/2011 07:09:33 None None 0
Going to X
QueueUpdate: DROPOFF21 JOB21 20 InProgress UnAllocated Goal
"x"
"MT-490" 12/19/2011 07:09:33 None None 0
QueueUpdate: DROPOFF21 JOB21 20 InProgress Allocated Goal "x"
"MT-490" 12/19/2011 07:09:33 None None 0
QueueUpdate: DROPOFF21 JOB21 20 InProgress Driving Goal "x"
"MT-490" 12/19/2011 07:09:33 None None 0
Arrived at X
QueueUpdate: DROPOFF21 JOB21 20 Completed None Goal "x"
"MT-490" 12/19/2011 07:09:33 12/19/2011 07:09:34 0
```

QueueShowRobot Example

Example

```
Queueshowrobot default echoit
QueueRobot: "Robot1" UnAvailable EStopPressed "echoit"
QueueRobot: "Robot2" UnAvailable Interrupted "echoit"
QueueRobot: "Robot3" UnAvailable InterruptedButNotYetIdle "echoit"
QueueRobot: "Robot4" Available Available "echoit"
QueueRobot: "Robot5" InProgress Driving "echoit"
QueueRobot: "Robot6" UnAvailable NotUsingEnterpriseManager "echoit"
QueueRobot: "Robot7" UnAvailable UnknownBatteryType "echoit"
QueueRobot: "Robot8" UnAvailable ForcedDocked "echoit"
QueueRobot: "Robot9" UnAvailable NotLocalized "echoit"
QueueRobot: "patrolbot" UnAvailable
Fault_Driving_Application_faultName ""
EndQueueShowRobot
```

QueueShowRobotLocal Example

Example

```
queueshowrobotlocal echoit
QueueRobot: "Robot1" UnAvailable EStopPressed "echoit"
EndQueueShowRobot
```

The above-described preferred embodiments are intended to illustrate the principles of the invention, but not to limit its scope. Various other embodiments, modifications and equivalents to these preferred embodiments may occur to those skilled in the art upon reading the present disclosure or practicing the claimed invention. Such variations, modifications and equivalents are intended to come within the scope of the invention and the appended claims.

What is claimed is:

1. A method of processing job requests on a job management system in a physical environment comprising the job management system and a fleet of mobile robots, the job management system including a queue manager, a memory and a network interface, the method comprising:
   a) prior to the queue manager receiving a job request, storing in the memory a map that (i) defines a floor plan corresponding to the physical environment, (ii) defines a virtual job location in respect to the floor plan, the virtual job location representing an actual job location in the physical environment, and (iii) associates a virtual job operation with the virtual job location, the virtual job operation representing an actual job operation in the physical environment;
   b) after the map is stored in the memory, receiving the job request by the queue manager, the job request including either the virtual job location on the map, or the virtual job operation on the map, but not both the virtual job location and the virtual job operation;
   c) with the queue manager, automatically selecting a mobile robot from the fleet to handle the received job request;
   d) transmitting one or more commands to the selected mobile robot via the network interface to cause the selected mobile robot (A) to automatically drive to the actual job location represented by the virtual job location, (B) to automatically execute the actual job operation represented by the virtual job operation, or (C) to automatically carry out both (A) and (B);
   e) determining the actual job location based on the map and the virtual job operation if the job request does not include the virtual job location; and
   f) determining the actual job operation based on the map and the virtual job location if the job request does not include the virtual job operation.

2. The method of claim 1, further comprising:
   a) storing in the memory a status profile for each mobile robot in the fleet, the status profile defining a current status for said each mobile robot;
   b) determining, based on the status profile for the selected mobile robot, that the current status for the selected mobile robot is compatible with the job request.

3. The method of claim 2, wherein the status profile comprises one or more of: a robot identifier, a robot position, a robot heading, a current robot speed, a current job identifier, a current job status, a current job location, a proximity to the current job location, a current job destination path, an estimated time of arrival, an estimated time of departure, a robot idle time, a robot performance level, a robot security level, a robot battery charge level, a robot payload status, a robot payload error condition, a robot cargo status, and a robot cargo capacity.

4. The method of claim 2, further comprising:
 a) establishing on the job management system a status-based preference criteria; and
 b) if two or more mobile robots in the fleet have current statuses that are compatible with the job request, selecting the mobile robot in accordance with the status-based preference criteria.

5. The method of claim 4, further comprising automatically comparing the status profiles for said two or more mobile robots to identify which of said two or more mobile robots has a more favorable status profile for the actual job location.

6. The method of claim 2, further comprising:
 a) receiving by the queue manager a specified time for performance of the job request; and
 b) determining by the queue manager, based on the status profile for the selected mobile robot, that the current status for the selected mobile robot is compatible with the specified time for performance.

7. The method of claim 2, further comprising:
 a) receiving by the queue manager a specified combination of job locations and job operations; and
 b) determining by the queue manager, based on the status profile for the selected mobile robot, that the current status for the selected mobile robot is compatible with the specified combination of job locations and job operations.

8. The method of claim 2, further comprising:
 a) receiving by the queue manager a specified route between job locations; and
 b) determining by the queue manager, based on the status profile for the selected mobile robot, that the current status for the selected mobile robot is compatible with the specified route.

9. The method of claim 2, further comprising:
 a) receiving by the queue manager a request to assign a particular mobile robot to handle the job request; and
 b) determining by the queue manager, based on the status profile for the particular mobile robot, that the current status for the particular mobile robot is compatible with the job request.

10. The method of claim 9, further comprising automatically selecting a different mobile robot for the job request if the status profile for the particular mobile robot is not compatible with the job request.

11. The method of claim 2, further comprising periodically receiving by the queue manager a status profile update for said selected mobile robot.

12. The method of claim 2, further comprising periodically receiving by the queue manager, a status profile update for every mobile robot in the fleet.

13. The method of claim 2, further comprising:
 a) receiving by the queue manager a specified priority for the job request; and
 b) determining by the queue manager, based on the status profile for the selected mobile robot, that the current status for the selected mobile robot is compatible with the specified priority.

14. The method of claim 1, further comprising:
 a) storing in the memory a configuration profile for each mobile robot in the fleet, the configuration profile defining a current configuration for said each mobile robot; and
 b) determining, based on the configuration profile for the selected mobile robot, that the current configuration for the selected mobile robot is compatible with the job request.

15. The method of claim 14, wherein the configuration profile comprises one or more of: a material handling capability, a material lifting capability, a material transporting capability, a manipulating capability, an object conveying capability, a measuring capability, a sensing capability, a pumping capability, a spraying capability, a vacuum capability, a drilling capability, a video recording capability, a sound recording capability, a sound producing capability, a navigation capability, a data input capability, a data output capability, a data communication capability, a printing capability, a displaying capability, a floor plan mapping capability, an energy absorption capability, an energy production capability, a maximum payload capability, a minimum payload capability, a maximum drive speed, a minimum drive speed, a maximum height, a minimum height, a location restriction, a zone restriction, a forbidden operation, a permitted operation, and a minimum clearance requirement.

16. The method of claim 14, further comprising:
 a) establishing on the job management system a configuration-based preference criteria; and
 b) if two or more mobile robots in the fleet have current configurations that are compatible with the job request, selecting the mobile robot in accordance with the configuration-based preference criteria.

17. The method of claim 16, further comprising automatically comparing the configuration profiles for said two or more mobile robots to identify which of said two or more mobile robots has a more favorable configuration profile for the actual job operation.

18. The method of claim 14, further comprising:
 a) receiving by the queue manager a specified time for performance of the job request; and
 b) determining by the queue manager, based on the configuration profile stored in the memory for the selected mobile robot, that the current configuration for the selected mobile robot is compatible with the specified time for performance.

19. The method of claim 14, further comprising:
 a) receiving by the queue manager a specified priority for the job request; and
 b) determining by the queue manager, based on the current configuration profile stored in memory for the selected mobile robot, that the current configuration for the selected mobile robot is compatible with the specified priority.

20. The method of claim 14, further comprising:
 a) receiving by the queue manager a specified combination of job locations and job operations; and
 b) determining by the queue manager, based on the current configuration profile stored in memory for the selected mobile robot, that the current configuration for the selected mobile robot is compatible with the specified combination.

21. The method of claim 14, further comprising:
 a) receiving by the queue manager a specified route that the selected mobile robot will use to drive to the actual job location; and
 b) determining by the queue manager, based on the current configuration profile stored in memory for the selected mobile robot, that the current configuration for the selected mobile robot is compatible with the specified route.

22. The method of claim 14, further comprising:
a) receiving by the queue manager a request to assign a particular mobile robot to handle the job request; and
b) determining by the queue manager, based on the current configuration profile stored in memory for the particular mobile robot, that the current configuration for the particular mobile robot is compatible with the job request.

23. The method of claim 22, further comprising automatically selecting a different mobile robot for the job request if the configuration profile for the particular mobile robot is not compatible with the job request.

24. The method of claim 14, further comprising periodically receiving by the queue manager a configuration profile update for said selected mobile robot.

25. The method of claim 14, further comprising periodically receiving by the queue manager, a configuration profile update for every mobile robot in the fleet.

26. The method of claim 1, further comprising:
a) receiving, by the network interface, a first planned path that the selected mobile robot plans to use to drive to the actual job location;
b) receiving, by the network interface, a second planned path that a second mobile robot in the fleet plans to use;
c) detecting, on the job management system, that the first planned path intersects the second planned path, that and
d) responsive to detecting the intersection, selecting by the queue manager a different mobile robot to handle the job request.

27. The method of claim 1, further comprising:
a) receiving, by the queue manager, a signal that no mobile robot in the fleet is available to handle the job request; and
b) automatically delaying, by the queue manager, selection of a mobile robot from the fleet to handle the job request until a mobile robot from the fleet becomes available.

28. The method of claim 1, further comprising:
c) receiving, by the queue manager, a signal that the selected mobile robot failed to handle the job request; and
d) automatically selecting, with the queue manager, a different mobile robot from the fleet to handle the job request, wherein the queue manager selects the different mobile robot based on the status profile and the configuration profile stored in the memory for the different mobile robot.

29. The method of claim 1, wherein the step of determining the actual job location is carried out on the job management system by the queue manager.

30. The method of claim 1, wherein the step of determining the actual job operation is carried out on the job management system by the queue manager.

31. The method of claim 1, further comprising:
a) copying the map and the virtual job operation from the queue manager to the selected mobile robot; and
b) the step of determining the actual job location is carried out on the selected mobile robot.

32. The method of claim 1, further comprising:
a) copying the map and the virtual job location from the queue manager to the selected mobile robot; and
b) the step of determining the actual job operation is carried out on the selected mobile robot.

33. A job management system for processing job requests in a physical environment comprising a fleet of mobile robots, the job management system comprising:
a) a memory;
b) a microprocessor coupled to the memory;
c) a queue manager, operable with the microprocessor and the memory to:
(i) prior to the queue manager receiving a job request, store in the memory a map that (A) defines a floor plan corresponding to the physical environment, (B) defines a virtual job location in respect to the floor plan, the virtual job location representing an actual job location in the physical environment, and (C) associates a virtual job operation with the virtual job location, the virtual job operation representing an actual job operation in the physical environment,
(ii) after the map is stored in the memory, receive the job request, the job request including either the virtual job operation on the map, or the virtual job location on the map, but not both the virtual job location and the virtual job operation,
(iii) automatically select a mobile robot from the fleet to handle the received job request,
(iv) automatically determine the actual job location based on the map and the virtual job operation if the job request does not include the virtual job location, and
(v) automatically determine the actual job operation based on the map and the virtual job location if the job request does not include the virtual job operation; and
d) a network interface to transmit one or more commands from the queue manager to the selected mobile robot to cause the selected mobile robot to (i) automatically drive to the actual job location represented by the virtual job location, (ii) automatically execute the actual job operation represented by the virtual job operation, or (iii) automatically carry out both d)(i) and d)(ii).

34. The job management system of claim 33, further comprising:
a) a status profile stored in the memory for each mobile robot in the fleet, the status profile defining a current status for said each mobile robot;
b) wherein the queue manager determines, based on the status profile for the selected mobile robot, that the current status for the selected mobile robot is compatible with the job request.

35. The job management system of claim 34, wherein the status profile comprises one or more of: a robot identifier, a robot position, a robot heading, a current robot speed, a current job identifier, a current job status, a current job location, a proximity to the current job location, a current job destination path, an estimated time of arrival, an estimated time of departure, a robot idle time, a robot performance level, a robot security level, a robot battery charge level, a robot payload status, a robot payload error condition, a robot cargo status, and a robot cargo capacity.

36. The job management system of claim 34, further comprising:
a) a status-based preference criteria; and
b) the queue manager is further configured to select the mobile robot in accordance with the status-based preference criteria if two or more mobile robots in the fleet have current statuses that are compatible with the job request.

37. The job management system of claim 36, wherein the queue manager automatically compares the status profiles for said two or more mobile robots to identify which of said two or more mobile robots has a more favorable status profile for the actual job location.

38. The job management system of claim 34, wherein:
   a) the queue manager receives a specified time for performance of the job request; and
   b) the queue manager determines, based on the status profile for the selected mobile robot, that the current status for the selected mobile robot is compatible with the specified time for performance.

39. The job management system of claim 34, wherein:
   a) the queue manager receives a specified combination of job locations and job operations; and
   b) the queue manager determines, based on the status profile for the selected mobile robot, that the current status for the selected mobile robot is compatible with the specified combination of job locations and job operations.

40. The job management system of claim 34, wherein:
   a) the queue manager receives a specified route between job locations; and
   b) the queue manager determines, based on the status profile for the selected mobile robot, that the current status for the selected mobile robot is compatible with the specified route.

41. The job management system of claim 34, wherein:
   a) the queue manager receives a request to assign a particular mobile robot to handle the job request; and
   b) the queue manager determines, based on the status profile for the particular mobile robot, that the current status for the particular mobile robot is compatible with the job request.

42. The job management system of claim 41, wherein the queue manager automatically selects a different mobile robot for the job request if the status profile for the particular mobile robot is not compatible with the job request.

43. The job management system of claim 34, wherein the status profile stored in the memory for said selected mobile robot is periodically updated.

44. The job management system of claim 34, wherein the status profile stored in the memory for every mobile robot in the fleet is periodically updated.

45. The job management system of claim 34, wherein:
   a) the queue manager receives a specified priority for the job request; and
   b) the queue manager determines, based on the status profile for the selected mobile robot, that the current status for the selected mobile robot is compatible with the specified priority.

46. The job management system of claim 33, wherein:
   a) the memory stores a configuration profile for each mobile robot in the fleet, the configuration profile defining a current configuration for said each mobile robot; and
   b) the queue manager determines, based on the configuration profile for the selected mobile robot, that the current configuration for the selected mobile robot is compatible with the job request.

47. The job management system of claim 46, wherein the configuration profile comprises one or more of: a material handling capability, a material lifting capability, a material transporting capability, a manipulating capability, an object conveying capability, a measuring capability, a sensing capability, a pumping capability, a spraying capability, a vacuum capability, a drilling capability, a video recording capability, a sound recording capability, a sound producing capability, a navigation capability, a data input capability, a data output capability, a data communication capability, a printing capability, a displaying capability, a floor plan mapping capability, an energy absorption capability, an energy production capability, a maximum payload capability, a minimum payload capability, a maximum drive speed, a minimum drive speed, a maximum height, a minimum height, a location restriction, a zone restriction, a forbidden operation, a permitted operation, and a minimum clearance requirement.

48. The job management system of claim 46, further comprising:
   a) a configuration-based preference criteria; and
   b) the queue management system is configured to select the mobile robot in accordance with the configuration-based preference criteria if two or more mobile robots in the fleet have current configurations that are compatible with the job request.

49. The job management system of claim 48, wherein the queue manager is further configured to compare the configuration profiles for said two or more mobile robots to identify which of said two or more mobile robots has a more favorable configuration profile for the actual job operation.

50. The job management system of claim 46, wherein:
   a) the queue manager receives a specified time for performance of the job request; and
   b) the queue manager determines, based on the configuration profile stored in the memory for the selected mobile robot, that the current configuration for the selected mobile robot is compatible with the specified time for performance.

51. The job management system of claim 46, wherein:
   a) the queue manager receives a specified priority for the job request; and
   b) the queue manager determines, based on the current configuration profile stored in memory for the selected mobile robot, that the current configuration for the selected mobile robot is compatible with the specified priority.

52. The job management system of claim 46, wherein:
   a) the queue manager receives a specified combination of job locations and job operations; and
   b) the queue manager determines, based on the current configuration profile stored in memory for the selected mobile robot, that the current configuration for the selected mobile robot is compatible with the specified combination.

53. The job management system of claim 46, wherein:
   a) the queue manager receives a specified route that the selected mobile robot will use to drive to the actual job location; and
   b) the queue manager determines, based on the current configuration profile stored in memory for the selected mobile robot, that the current configuration for the selected mobile robot is compatible with the specified route.

54. The job management system of claim 46, wherein:
   a) the job request includes a request to assign a particular mobile robot to handle the job request; and
   b) the queue manager determines, based on the current configuration profile stored in memory for the particular mobile robot, that the current configuration for the particular mobile robot is compatible with the job request.

55. The job management system of claim 54, wherein the queue manager automatically determines a different mobile robot for the job request if the configuration profile for the particular mobile robot is not compatible with the job request.

56. The job management system of claim 46, wherein the configuration profile stored in the memory for said selected mobile robot is periodically updated.

57. The job management system of claim 46, wherein the configuration profiles stored in the memory for every mobile robot in the fleet are periodically updated.

58. The job management system of claim 33, wherein:
a) the job management system receives a first planned path that the selected mobile robot plans to use to drive to the actual job location;
b) the job management system receives a second planned path that a second mobile robot in the fleet plans to use;
c) the job management system detects that the first planned path intersects the second planned path, that and
d) responsive to detecting the intersection, the queue manager selects a different mobile robot to handle the job request.

59. The job management system of claim 33, wherein:
a) the queue manager receives a signal that no mobile robot in the fleet is available to handle the job request; and
b) the queue manager automatically delays selection of a mobile robot from the fleet to handle the job request until a mobile robot from the fleet becomes available.

60. The job management system of claim 33, wherein:
a) the queue manager receives a signal that the selected mobile robot failed to handle the job request; and
b) the queue manager automatically selects a different mobile robot from the fleet to handle the job request.

61. A non-transitory computer-readable storage medium with an executable program for processing job requests in a physical environment comprising a fleet of mobile robots, wherein the executable program comprises program instructions to cause one or more microprocessors on a computer system to:
a) prior to receiving a job request, store in a memory device on the computer system a map that (i) defines a floor plan corresponding to the physical environment, (ii) defines a virtual job location in respect to the floor plan, the virtual job location representing an actual job location in the physical environment, and (iii) associates a virtual job operation with the virtual job location, the virtual job operation representing an actual job operation in the physical environment;
b) after storing the map in the in the memory device, receive on the computer system a job request, the job request including either the virtual job operation on the map, or the virtual job location on the map, but not both the virtual job location and the virtual job operation;
c) automatically select a mobile robot from the fleet to handle the received job request;
d) automatically determine the actual job location based on the map and the virtual job operation if the job request does not include the virtual job location;
e) automatically determine the actual job operation based on the map and the virtual job location if the job request does not include the virtual job operation; and
f) transmit one or more commands from the computer system to the selected mobile robot to cause the selected mobile robot to (i) automatically drive to the actual job location represented by the virtual job location, (ii) automatically execute the actual job operation represented by the virtual job operation, or (iii) automatically carry out both f)(i) and f)(ii).

62. The non-transitory computer-readable storage medium of claim 61, wherein the executable program further includes program instructions to cause said one or more microprocessors to:
a) store a status profile in the memory for each mobile robot in the fleet, the status profile defining a current status for said each mobile robot; and
b) determine, based on the status profile for the selected mobile robot, that the current status for the selected mobile robot is compatible with the job request.

63. The non-transitory computer-readable storage medium of claim 62, wherein the status profile comprises one or more of: a robot identifier, a robot position, a robot heading, a current robot speed, a current job identifier, a current job status, a current job location, a proximity to the current job location, a current job destination path, an estimated time of arrival, an estimated time of departure, a robot idle time, a robot performance level, a robot security level, a robot battery charge level, a robot payload status, a robot payload error condition, a robot cargo status, and a robot cargo capacity.

64. The non-transitory computer-readable storage medium of claim 62, wherein the executable program further includes program instructions to cause said one or more microprocessors to:
a) store in the memory a status-based preference criteria; and
b) select the mobile robot in accordance with the status-based preference criteria if two or more mobile robots in the fleet have current statuses that are compatible with the job request.

65. The non-transitory computer-readable storage medium of claim 64, wherein the executable program further includes program instructions to cause said one or more microprocessors to compare the status profiles for said two or more mobile robots to identify which of said two or more mobile robots has a more favorable status profile for the actual job location.

66. The non-transitory computer-readable storage medium of claim 61, wherein the executable program further includes program instructions to cause said one or more microprocessors to:
a) store in the memory a configuration profile for each mobile robot in the fleet, the configuration profile defining a current configuration for said each mobile robot; and
b) determine, based on the configuration profile for the selected mobile robot, that the current configuration for the selected mobile robot is compatible with the job request.

67. The non-transitory computer-readable storage medium of claim 66, wherein the configuration profile comprises one or more of: a material handling capability, a material lifting capability, a material transporting capability, a manipulating capability, an object conveying capability, a measuring capability, a sensing capability, a pumping capability, a spraying capability, a vacuum capability, a drilling capability, a video recording capability, a sound recording capability, a sound producing capability, a navigation capability, a data input capability, a data output capability, a data communication capability, a printing capability, a displaying capability, a floor plan mapping capability, an energy absorption capability, an energy production capability, a maximum payload capability, a minimum payload capability, a maximum drive speed, a minimum drive speed, a maximum height, a minimum height, a location restriction, a zone restriction, a forbidden operation, a permitted operation, and a minimum clearance requirement.

68. The non-transitory computer-readable storage medium of claim 66, wherein the executable program further includes program instructions to cause said one or more microprocessors to:
   a) store in the memory a configuration-based preference criteria; and
   b) select the mobile robot in accordance with the configuration-based preference criteria if two or more mobile robots in the fleet have current configurations that are compatible with the job request.

69. The non-transitory computer-readable storage medium of claim 68, wherein the executable program further includes program instructions to cause said one or more microprocessors to compare the configuration profiles for said two or more mobile robots to identify which of said two or more mobile robots has a more favorable configuration profile for the actual job operation.

* * * * *